(12) United States Patent
Igarashi et al.

(10) Patent No.: US 7,526,070 B2
(45) Date of Patent: Apr. 28, 2009

(54) X-RAY CT APPARATUS COLLIMATOR, METHOD OF MANUFACTURING THE X-RAY CT APPARATUS COLLIMATOR, AND X-RAY CT APPARATUS

(75) Inventors: Kenji Igarashi, Utsunomiya (JP); Masaharu Shimizu, Nasushiobara (JP); Akiji Wakabayashi, Otawara (JP); Yasuo Saito, Nasushiobara (JP); Machiko Iso, Nasushiobara (JP); Tsuguo Kishi, Yokohama (JP); Shigeru Sakuta, Urayasu (JP); Masaru Kitamura, Yokohama (JP); Ryuhachiro Doji, Yokohama (JP); Hideki Ide, Yokohama (JP); Shuya Nambu, Nasushiobara (JP); Masahiko Yamazaki, Utsunomiya (JP); Katsuya Yamada, Kamakura (JP); Yasutada Nakagawa, Yokohama (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/403,813

(22) Filed: Apr. 14, 2006

(65) Prior Publication Data

US 2006/0233298 A1  Oct. 19, 2006

(30) Foreign Application Priority Data

Apr. 15, 2005 (JP) .............................. 2005-118772

(51) Int. Cl.
*G21K 1/02* (2006.01)
*G21K 1/00* (2006.01)
(52) U.S. Cl. ........................... 378/149; 378/147; 378/19

(58) Field of Classification Search .................... 378/7, 378/19, 147, 149, 154
See application file for complete search history.

(56) References Cited

U.S. PATENT DOCUMENTS

| 5,357,553 | A | | 10/1994 | Ferlic et al. |
| 5,648,997 | A | * | 7/1997 | Chao ........................ 378/98.4 |
| 5,965,893 | A | * | 10/1999 | Tonami et al. ......... 250/370.11 |
| 5,991,357 | A | * | 11/1999 | Marcovici et al. ............. 378/19 |
| 6,181,767 | B1 | * | 1/2001 | Harootian .................... 378/19 |
| 6,363,136 | B1 | * | 3/2002 | Flisikowski et al. ......... 378/154 |
| 2002/0064252 | A1 | * | 5/2002 | Igarashi et al. ................ 378/19 |

(Continued)

FOREIGN PATENT DOCUMENTS

DE  197 50 935  6/1999

(Continued)

*Primary Examiner*—Edward J Glick
*Assistant Examiner*—Anastasia Midkiff
(74) *Attorney, Agent, or Firm*—Oblon, Spivak, McClelland, Maier & Neustadt, P.C.

(57) ABSTRACT

The angle of each collimator plate with respect to an X ray focal point is determined by fitting the collimator plate in grooves formed in upper and lower supports each having an integral structure. In addition, the warpage of each collimator plate is corrected and its flatness is maintained by fitting the periphery of the collimator plate which is on the X ray detector side in a corresponding groove of an abutment plate provided on the X ray detection surface side of the upper and lower supports. Furthermore, each collimator plate is supported by the corresponding grooves of the upper and lower supports and the corresponding groove of the abutment plate on at least three sides.

22 Claims, 31 Drawing Sheets

U.S. PATENT DOCUMENTS

2003/0155518 A1* 8/2003 Francke ............... 250/385.1
2005/0117697 A1* 6/2005 Yasunaga et al. ............ 378/19

FOREIGN PATENT DOCUMENTS

| | | |
|---|---|---|
| DE | 100 11 877 | 9/2001 |
| JP | 7-77580 | 3/1995 |
| JP | 2002082175 A * | 3/2002 |
| JP | 2002-162472 | 6/2002 |

* cited by examiner

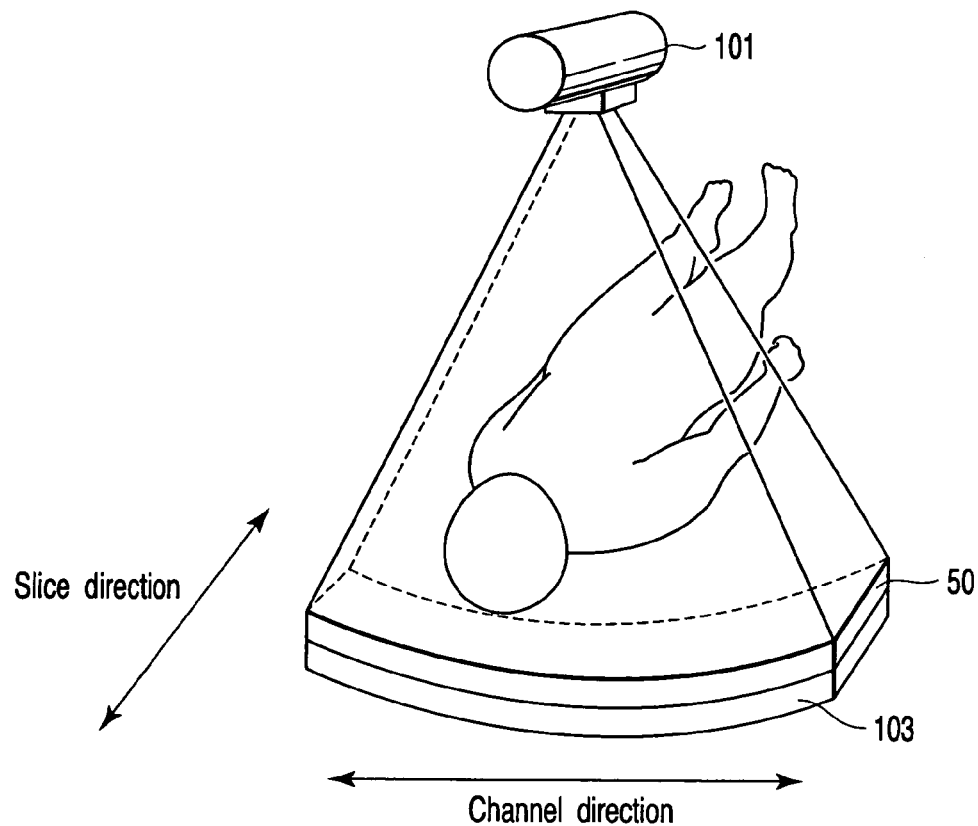
F I G. 2 B
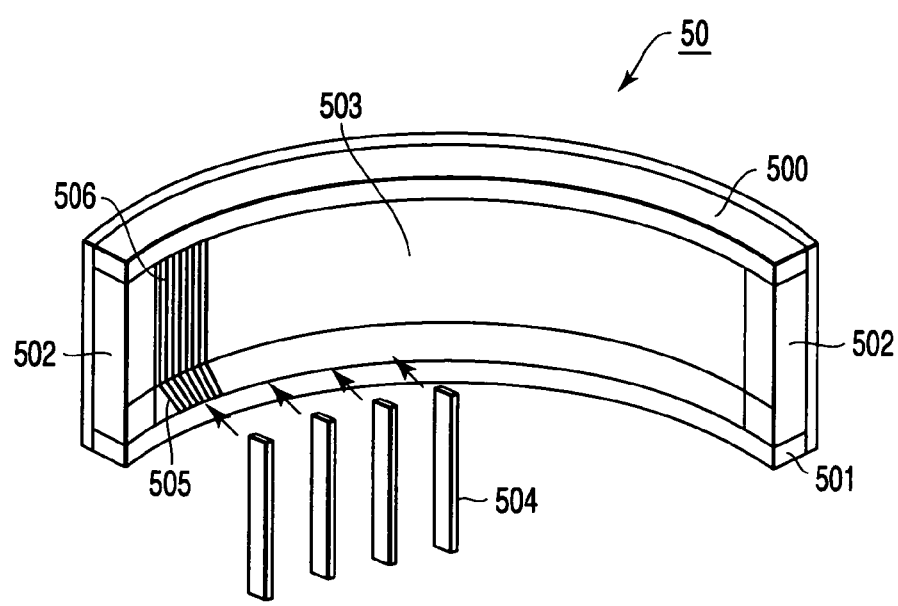
F I G. 3

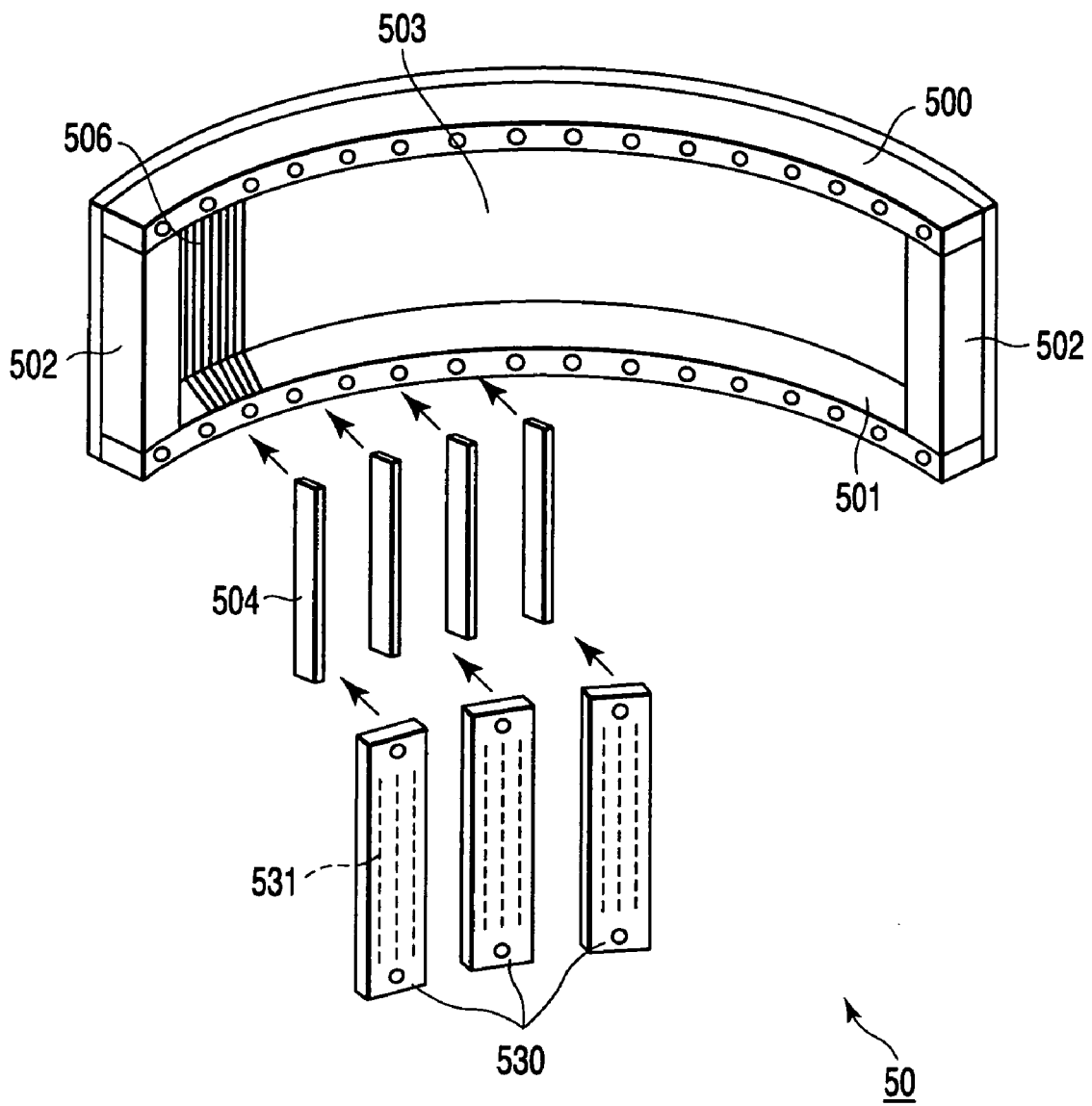
F I G. 20 A

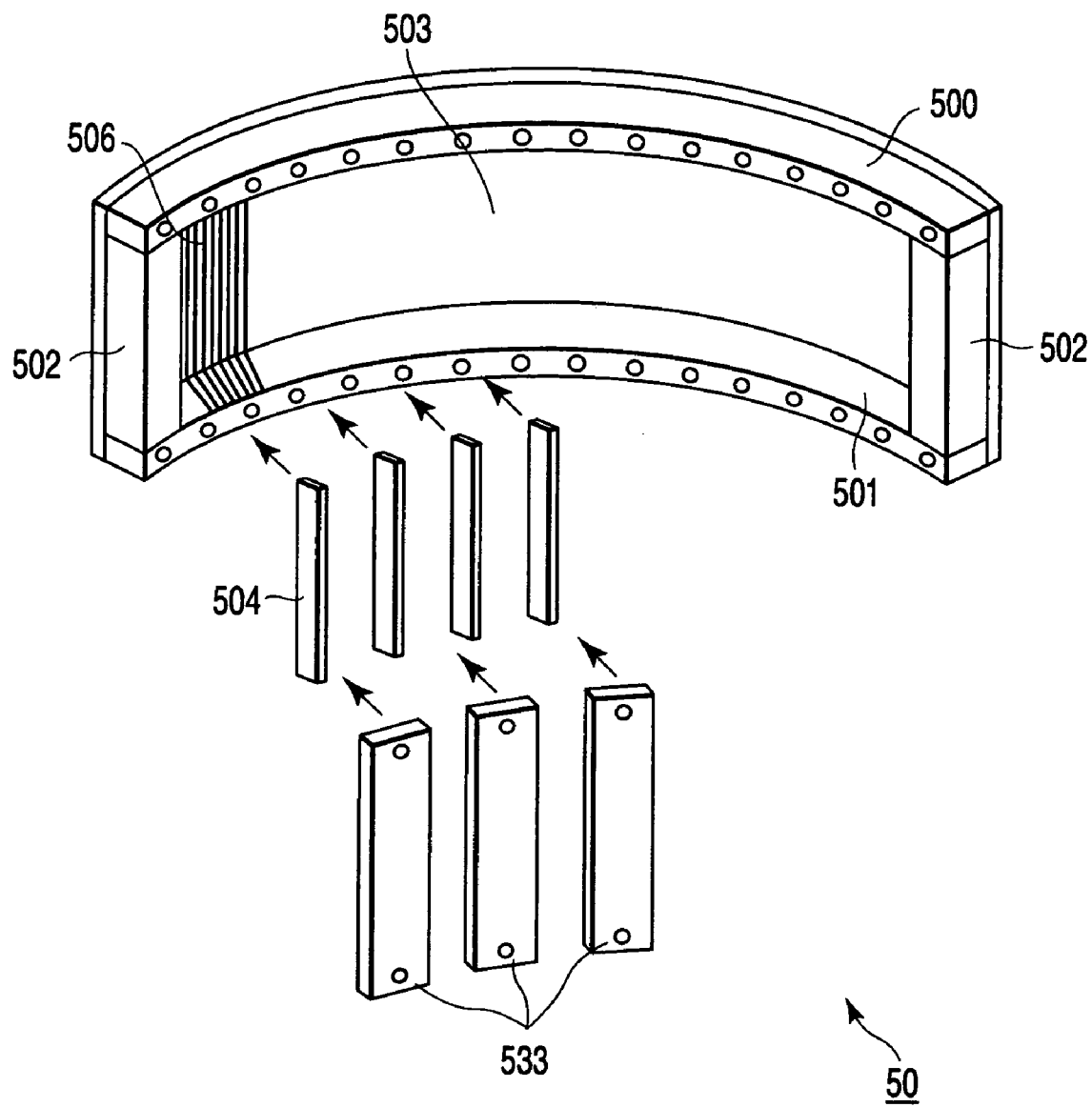
F I G. 22

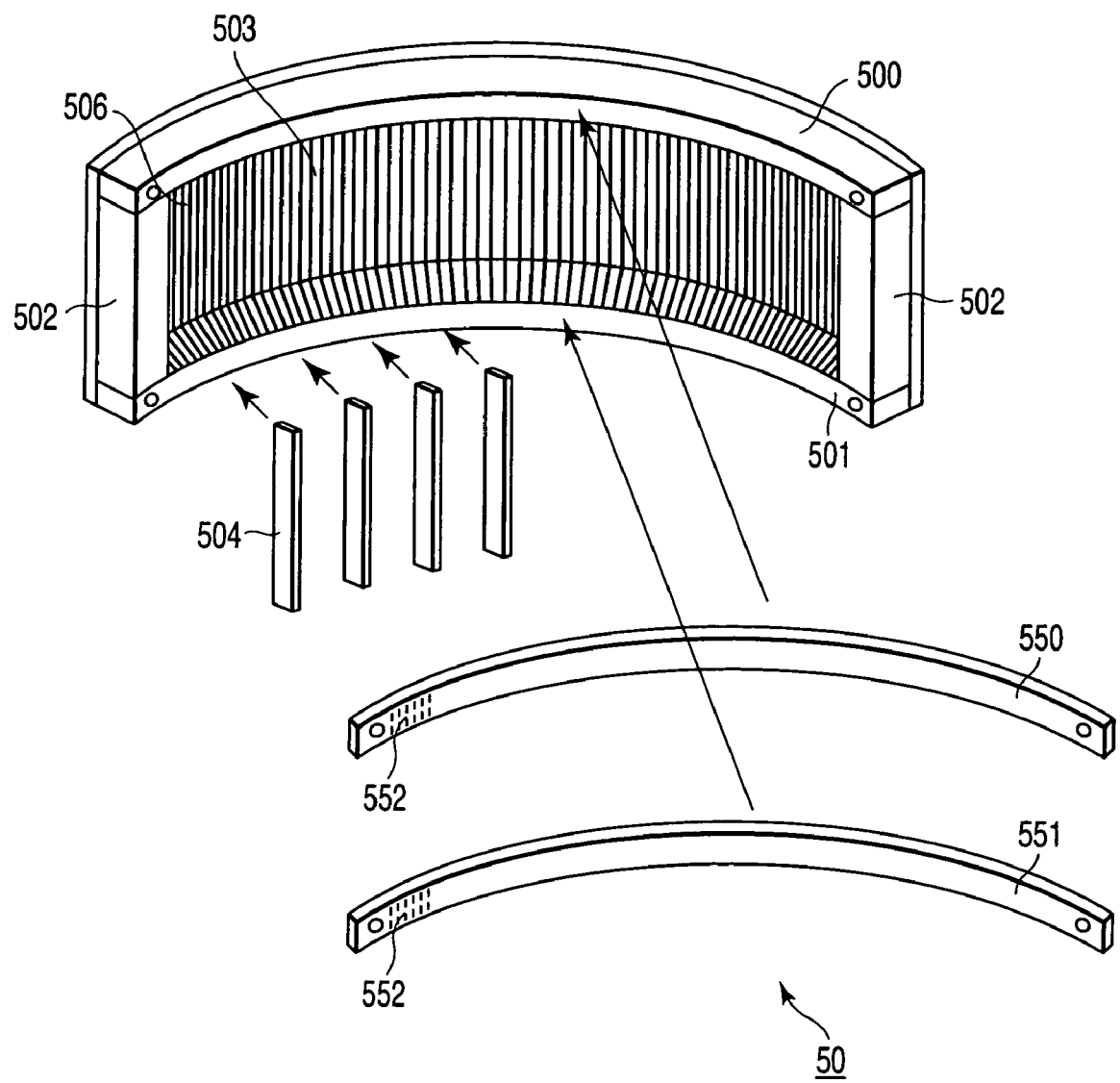
F I G. 29

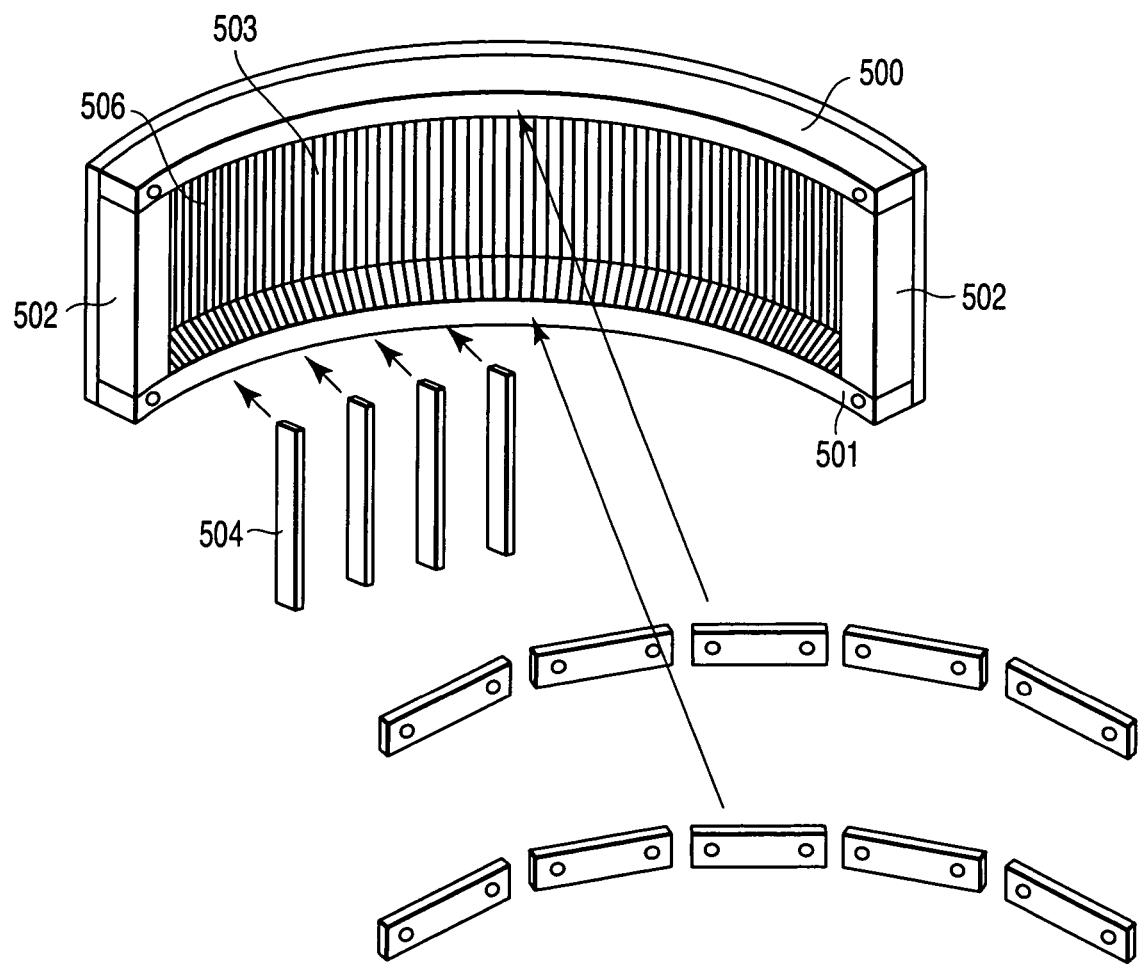
F I G. 3 4

X-RAY CT APPARATUS COLLIMATOR, METHOD OF MANUFACTURING THE X-RAY CT APPARATUS COLLIMATOR, AND X-RAY CT APPARATUS

CROSS-REFERENCE TO RELATED APPLICATIONS

This application is based upon and claims the benefit of priority from prior Japanese Patent Application No. 2005-118772, filed Apr. 15, 2005, the entire contents of which are incorporated herein by reference.

BACKGROUND OF THE INVENTION

1. Field of the Invention

The present invention relates to a collimator used for an X-ray CT (Computer Tomography) apparatus, a method of manufacturing the collimator, and an X-ray CT apparatus having the collimator.

2. Description of the Related Art

As is well known, an X-ray CT apparatus is designed to obtain an image (tomographic image) by calculating (reconstructing) the X-ray absorptance of tissue such as an organ as an index called a CT value with reference to the X-ray absorptance of water on the basis of the amount of X-rays absorbed by a subject.

This X ray CT apparatus is provided with a collimator on, for example, the X ray incident side of an X ray detector to reshape the shape of an X ray beam striking each X ray detection element and to remove scattered X rays. FIG. 1A shows an example of the arrangement of a conventional collimator having an integral structure (to be referred to as an "integral collimator" hereinafter). As shown in FIG. 1A, the integral collimator has upper and lower arcuate supports arranged side by side in the slice direction along the body axis of a subject. Pairs of upper and lower grooves are formed in the upper and lower supports so as to allow the insertion of collimator plates therein such that the respective plates face an X ray focal point (which is assumed to be the emission point of an X ray source). Flattened collimator plates are inserted in these grooves. An adhesive is then applied to the portions of the plates which are inserted in the grooves and is cured, thereby forming a collimator as an integral structure. The collimator plates are supported by the grooves of the upper and lower supports, and reshape incident X rays without degrading the warpage of each plate owing to its rigidity.

Assume that such an integral collimator comprises, for example, collimator plates each having a length of less than 100 mm in the slide direction in an X-ray CT apparatus. In this case, if flattening processing is performed for each collimator plate in advance, a collimator with little warpage on the 20 µm order can be formed with only the rigidity of each collimator plate.

The recent trend is to develop X-ray CT apparatuses with wider detection ranges in the slice direction. In an X-ray CT apparatus having 256 rows of multi-slice detectors which has currently been developed, the detection range in the slice direction is assumed to be about four times that in existing X-ray CT apparatuses. For this reason, according to the arrangement of a conventional integral collimator, it is difficult to maintain the flatness and warpage of each collimator plate with only the rigidity of each collimator plate. As a consequence, when each detector (detector unit) is to be mounted, alignment cannot be performed, and the solid angle of an X-ray beam striking each X-ray detection element cannot be properly limited, resulting in failure to acquire an appropriate tomographic image.

In order to solve this problem, for example, as shown in FIG. 1B, there has been proposed a collimator having a module structure (to be referred to as a "module type collimator" hereinafter) which covers about 20 channels of a detector. As shown in FIG. 1B, a plurality of such module type collimators are arranged to cover the entire detection surface of the X-ray detector along the channel direction. The module type collimator has front and rear supports, in each of which grooves in which collimator plates are to be inserted are formed. These grooves are formed in the front and rear supports at different pitches because collimator plates need to face the X-ray focal point. By inserting collimator plates in the pairs of grooves in the front and rear supports, the collimator plates form an arrangement widening toward the end. As a result, all the collimator plates are formed to face the X-ray focal point.

Such a module type collimator is assembled while adjusting the squareness with respect to an end face of each support or the reference surface of the central plate, thereby forming a module type collimator set at a correct position opposing the X-ray focal point. It has been confirmed that in even a region where the detection range of each collimator plate in the slice direction is about 200 mm or more and hence it is difficult to flatten collimator plates, warpage is corrected by inserting plates in the grooves formed in the front and rear supports in the slice direction, and a collimator which maintains flatness as in existing collimators can be formed. As a consequence, alignment with the detector can be done.

In the above module type collimator as well, for example, the following problem arises.

In the module type collimator, factors that unstabilize the mount surface of the detector module on which the collimator is mounted cannot be eliminated. Even if, for example, a dust particle on the 10 µm order exists on the mount surface, the X-ray focal point at the position about 1 m ahead of the dust particle is enlarged and shifted. Therefore, steps are produced in continuity that connects the X-ray focal point at the joint portions between the module type collimators. As a consequence, when the polar response characteristic, i.e., the X-ray foal point, shifts over time, an impermissible unbalance amount, which cannot be neglected, is produced in variation components of shadow on the detector, resulting in the production of artifacts in an image.

BRIEF SUMMARY OF THE INVENTION

The present invention has been made in consideration of the above situation, and has as its object to provide an X-ray CT apparatus collimator, a method of manufacturing the collimator, and an X-ray CT apparatus which can realize proper X-ray collimation by maintaining the flatness of each collimator plate without losing the continuity of the X-ray focal point.

According to an aspect of the present invention, there is provided an X ray CT apparatus which comprises: an X ray exposing unit which radiates X rays; an X ray detection unit which is placed to face the X ray exposing unit through a subject and detects X rays incident to a detection surface; and a collimator unit (50) which is placed on the X ray incident side of an X ray detector to remove scattered X rays and includes a plurality of collimator plates and a support unit, the plurality of collimator plates being arranged along a predetermined direction, and the support unit supporting at least three sides of each of the collimator plates such a manner that a surface of each of the collimator plates is substantially parallel to an X ray incident direction from the X ray exposing unit to the detection surface.

According to another aspect of the present invention, there is provided an X ray CT apparatus collimator manufacturing method of manufacturing a collimator which is used for an X ray CT apparatus comprising an X ray exposing unit which radiates X rays and an X ray detection unit which is placed to face the X ray exposing unit through a subject and detects X rays striking a detection surface, and is provided on the detection surface to remove scattered X rays, which comprises: assembling, by using side surface members, a first support unit including a plurality of first grooves formed along an X ray incident direction from the X ray exposing unit to the detection surface and a second support unit including a plurality of second grooves formed along the X ray incident direction from the X ray exposing unit to the detection surface so as to correspond to said plurality of first grooves; fixing, to the detection surface side of the first support unit and second support unit, a first support unit including a plurality of third grooves for fitting of peripheries of the collimator plates fitted in the first grooves and the second grooves which face each other which are located on the detection surface side; fitting collimator plates in the first grooves, the second grooves, and the third grooves which face each other; and bonding said each collimator plate to the first groove, the second groove, and the third groove which correspond to said each collimator plate.

According to yet another aspect of the present invention, there is provided an X-ray CT apparatus collimator manufacturing method of manufacturing a collimator which is used for an X-ray CT apparatus comprising an X-ray exposing unit which exposes X-rays and an X-ray detection unit which is placed to face the X-ray exposing unit through a subject and detects X-rays striking a detection surface, and is provided on the detection surface to remove scattered X-rays, which comprises: assembling, by using side surface members, a first support unit including a plurality of first grooves formed along an X-ray incident direction from the X-ray exposing unit to the detection surface and a second support unit including a plurality of second grooves formed along the X-ray incident direction from the X-ray exposing unit to the detection surface so as to correspond to said plurality of first grooves; fixing, to the detection surface side of the first support unit and second support unit, a first support unit including a plurality of third grooves for fitting of peripheries of the collimator plates fitted in the first grooves and the second grooves corresponding to each other which are located on the detection surface side; fixing the second support including slits which allow the collimator plates fitted in the first grooves and the second grooves which face each other to pass through the slits and support peripheries of the collimator plates which are on an X-ray incident side to the X-ray incident side of the first support unit and the second support unit; fitting collimator plates in the first grooves, the second grooves, and the third grooves which face each other upon making the collimator plates pass through the slits; and bonding the collimator plates to the first grooves, the second grooves, the third grooves, and the slits which correspond to each other.

BRIEF DESCRIPTION OF THE SEVERAL VIEWS OF THE DRAWING

FIG. 2B is a schematic view for explaining the layout of a detector-side collimator 50;

FIG. 3 is a view for explaining the arrangement of the detector-side collimator 50;

FIG. 20A is a view showing the arrangement of the detector-side collimator 50 possessed by the X-ray CT apparatus 10 according to a fourth embodiment;

FIG. 22 is a view showing the arrangement of the detector-side collimator 50 according to a modified example of the fourth embodiment;

FIG. 29 is a view showing the arrangement of the detector-side collimator 50 possessed by the X-ray CT apparatus 10 according to a sixth embodiment;

FIG. 34 is a view showing the arrangement of the detector-side collimator 50 according to another modified example of the sixth embodiment.

DETAILED DESCRIPTION OF THE INVENTION

Figure 1A:
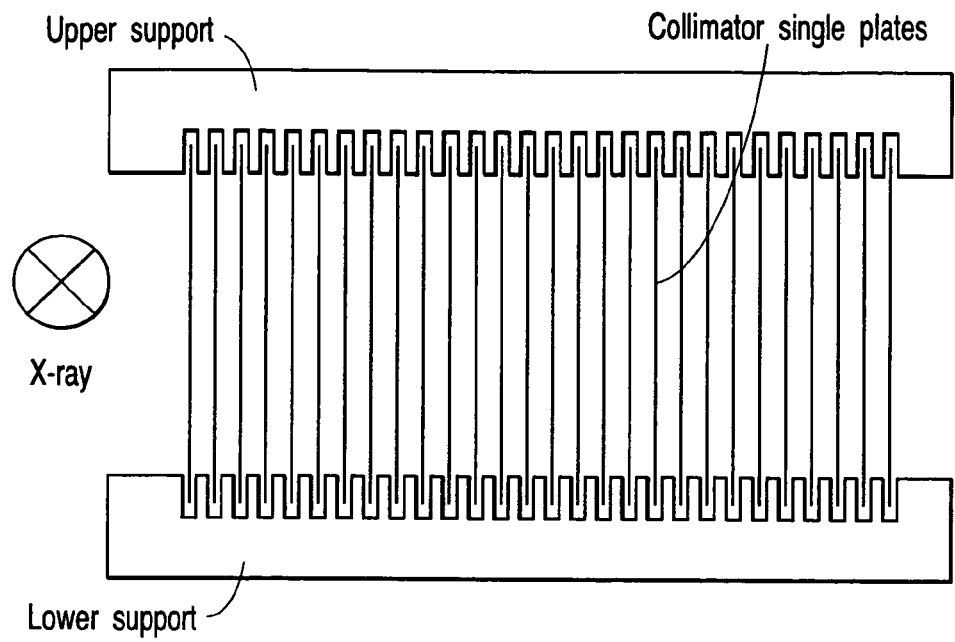
FIG. 1A is a view for explaining the arrangement of a conventional integral collimator.

The first and second embodiments of the present invention will be described below with reference to the views of the accompanying drawing. Note that the same reference numerals in the following description denote constituent elements having substantially the same functions and arrangements, and a repetitive description thereof will be made only when required.

FIRST EMBODIMENT

Figure 2A:
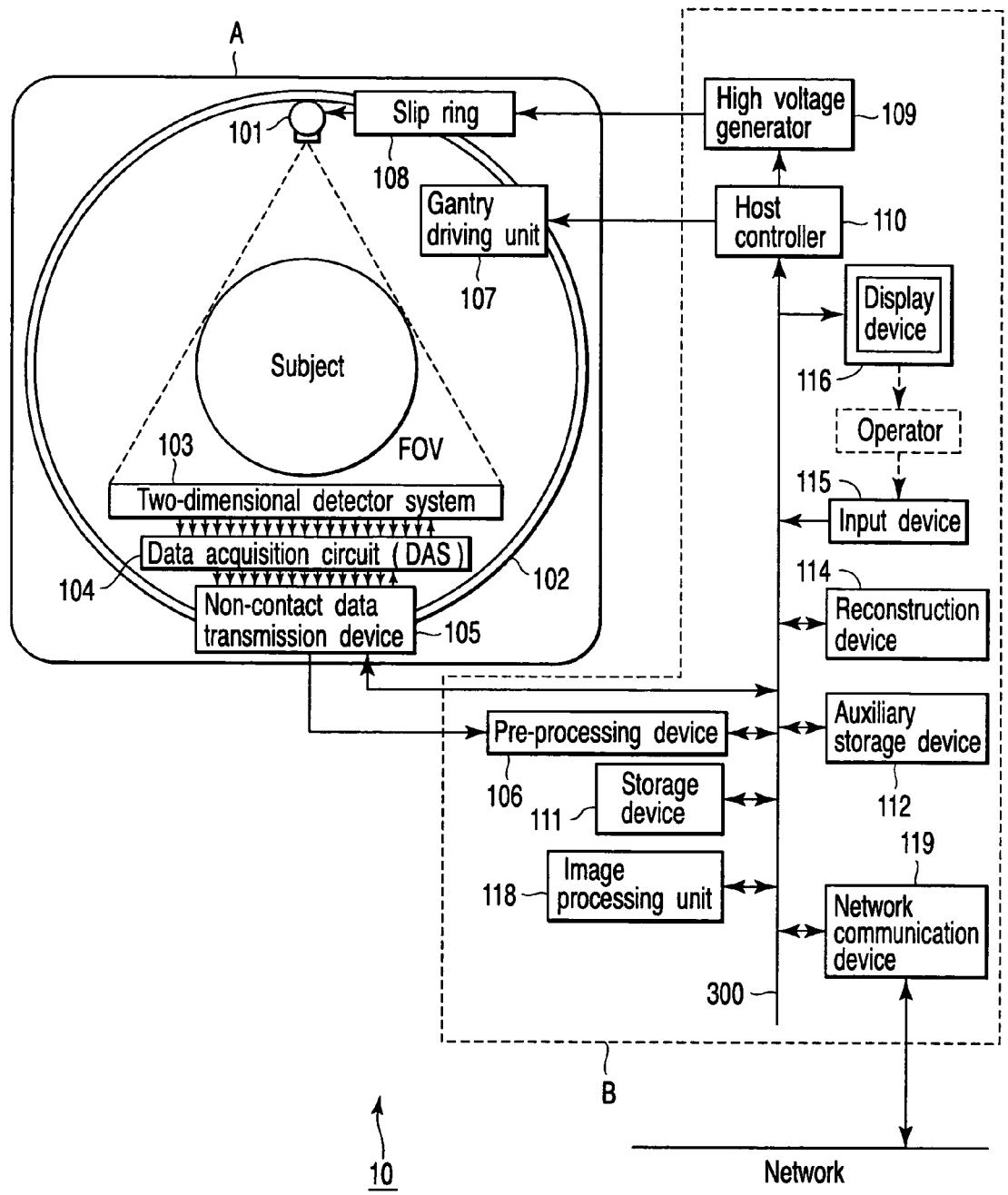
FIG. 2A is a block diagram showing the arrangement of an X-ray CT apparatus 10 according to an embodiment.

FIG. 2A is a block diagram showing the arrangement of an X-ray CT apparatus 10 according to this embodiment. As shown in FIG. 2A, the X-ray CT apparatus 10 comprises an imaging system A and a processing/display system B. The constituent elements of these systems will be described below.

The imaging system A acquires projection data (or raw data) by applying X-rays to a subject and detecting X-rays transmitted through the subject. Note that the imaging systems of X-ray CT apparatuses include various types, e.g., a rotate/rotate type in which an X-ray tube and a two-dimensional detector system rotate together around a subject, a stationary/rotate type in which many detection elements are arrayed in the form of a ring, and only an X-ray tube rotates around a subject, and a type which electronically moves the position of an X-ray source onto a target by deflecting an electron beam. The present invention can be applied to all types. In this case, the rotate/rotate type X-ray CT apparatus, which is currently the mainstream, will be exemplified.

Figure 1B:
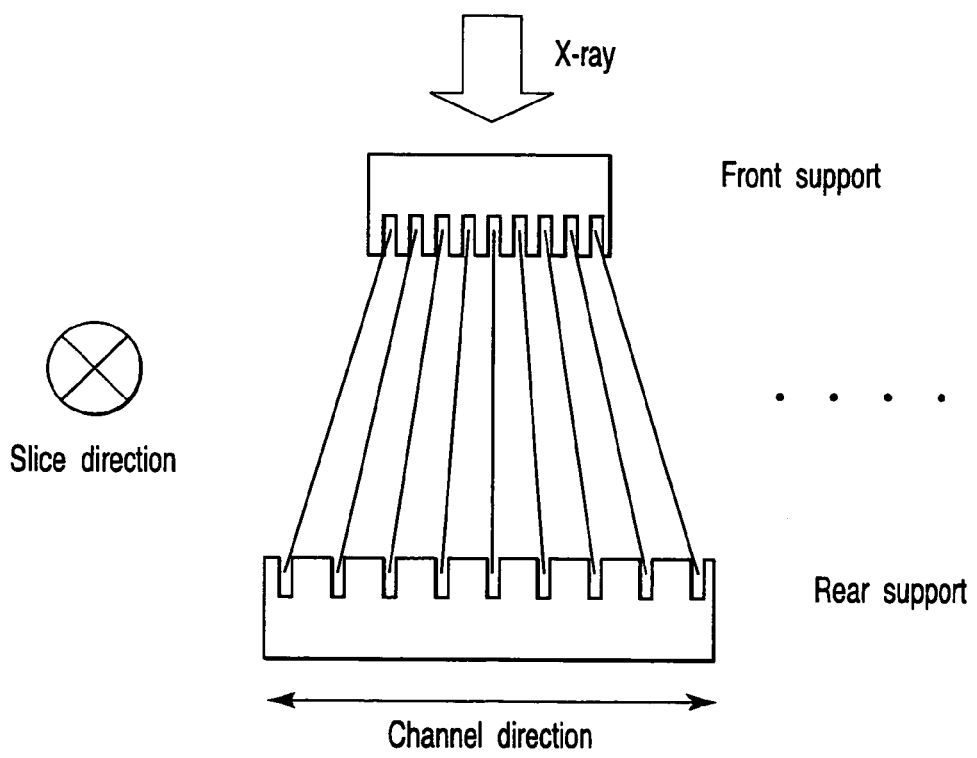
FIG. 1B is a view for explaining the arrangement of a module type collimator.

As shown in FIG. 2A, the imaging system A has an X-ray tube 101, rotating ring 102, two-dimensional detector system 103, data acquisition circuit (DAS) 104, non-contact data transmission device 105, gantry driving unit 107, slip ring 108, X-ray tube side collimator (not shown in FIG. 2A), and X-ray detector-side collimator (not shown in FIG. 1).

The X-ray tube 101 is a vacuum tube which generates X-rays, and is amounted on the rotating ring 102. Power (a tube current or tube voltage) required for the emission of X-rays is supplied from a high voltage generator 109 to the X-ray tube 101 through the slip ring 108. The X-ray tube 101 exposes X-rays to a subject placed in an effective field of view FOV by accelerating electrons using the applied high voltage and making them collide with the target.

An X-ray tube side collimator (not shown) which reshapes an X-ray beam exposed from the X-ray tube 101 into a cone shape (quadrangular pyramidal shape) or a fan beam shape is provided between the X-ray tube 101 and the subject.

The two-dimensional detector system 103 is a detector system which detects X-rays transmitted through the subject, and is mounted on the rotating ring 102 to face the X-ray tube 101. In the two-dimensional detector system 103, a plurality of detection elements comprising combinations of scintillators and photodiodes form a detection surface, and are arrayed in the form of a matrix in the body axis direction of the subject (slice direction) and the channel direction perpendicular thereto.

As schemes of converting incident X-rays into electric charges in each detection element, a direct conversion scheme and an indirect conversion scheme are available. This embodiment is not limited to either of the schemes.

The X-ray tube 101 and the detector system 103 are mounted on the rotating ring 102. The rotating ring 102 is driven by the gantry driving unit 107 and rotates around the subject at a high speed of one rotation per second.

The data acquisition circuit (DAS) 104 has a plurality of data acquisition element rows on which DAS chips are arrayed. The data acquisition circuit (DAS) 104 receives an enormous amount of data (M×N-channel data per view will be referred to as "raw data" hereinafter) associated with all M×N channels, which are detected by the two-dimensional detector system 103, performs amplification processing, A/D conversion processing, and the like, and transmits the resultant data altogether to a data processing unit on the fixed side through the non-contact data transmission device 105 using optical communication.

The X-ray detector-side collimator reshapes an X-ray beam striking each detection element of the two-dimensional detector system 103, and is provided on the X-ray incident side of the two-dimensional detector system 103.

The processing/display system B will be described next. The processing/display system B comprises a pre-processing device 106, the high voltage generator 109, a host controller 110, a storage device 111, an auxiliary storage device 112, a reconstruction device 114, an input device 115, a display device 116, an image processing unit 118, a network communication device 119, and a data/control bus 300.

The pre-processing device 106 receives raw data from the DAS 104 through the non-contact data transmission device 105, and executes sensitivity correction and X-ray intensity correction. Note that the raw data pre-processed by the pre-processing device 106 will be referred to as "projection data".

The gantry driving unit 107 performs, for example, driving control to rotate the X-ray tube 101 and the two-dimensional detector system 103 together around a central axis parallel to the body axis direction of the subject inserted in the opening for diagnosis.

The high voltage generator 109 is a device which supplies power necessary for the emission of X-rays to the X-ray tube 101 through the slip ring 108, and comprises a high voltage transformer, filament heating converter, rectifier, high voltage switch, and the like. The high voltage generator 109 applies a high voltage to the X-ray tube 101 through the slip ring 108.

The host controller 110 performs overall control associated with various kinds of processing, e.g., imaging processing, data processing, and image processing.

The storage device 111 stores image data such as acquired raw data, projection data, and CT image data.

The reconstruction device 114 generates reconstructed image data corresponding to a predetermined number of slices by performing reconstruction processing for projection data on the basis of predetermined reconstruction parameters (e.g., a reconstruction area size, a reconstruction matrix size, and a threshold for the extraction of a region of interest). In general, reconstruction processing includes cone beam reconstruction (the Feldkamp method, ASSR method, and the like) and fan beam reconstruction. Any technique can be implemented.

The input device 115 is a device which comprises a keyboard, various kinds of switches, a mouse, and the like, and can input various kinds of scan conditions such as a slice thickness and the number of slices through an operator.

The image processing unit 118 performs image processing for display, e.g., window conversion and RGB processing, for the reconstructed image data generated by the reconstruction device 114, and outputs the resultant data to the display device 116. The image processing unit 118 generates a so-called pseudo three-dimensional image such as a tomographic image of an arbitrary slice, a projection image from an arbitrary direction, or a three-dimensional surface image on the basis of an instruction from the operator, and outputs the generated image data to the display device 116. The output image data is displayed as an X-ray CT image on the display device 116.

The network communication device 119 transmits/receives various kinds of data to/from another device or a network system such as an RIS (Radiology Information System) through a network.

The data/control bus 300 is a signal line for connecting the respective units to each other and transmitting/receiving various kinds of data, control signals, address information, and the like.

(Collimator)

The details of the X-ray detector-side collimator will be described next. This X-ray detector-side collimator has a structure which ensures to maintain the continuity of an X-ray focal point and the flatness of each collimator plate even if the detection range is relatively large in the slice direction.

FIG. 2B is a view for explaining an outline of a form of installing an X ray detector side collimator 50. As shown in FIG. 2B, the X ray detector side collimator 50 is installed along the shape of the two dimensional detector system 103 (i.e., in an arcuate shape) on the X ray incident side of the two dimensional detector system 103.

FIG. 3 is a view for explaining the arrangement of the X-ray detector-side collimator 50. As shown in FIG. 3, the X-ray detector-side collimator 50 has an upper support 500, a lower support 501, side surface members 502, an abutment plate 503, and collimator plates 504. Note that with regard to the supports 500 and 501, the terms "upper" and "lower" are defined with reference to the upper and lower sides of a subject placed along the slice direction. These terms are defined for the sake of convenience, and hence the distinction between the terms "upper" and "lower" concerning the supports is not essential.

The upper support 500 and the lower support 501 each are formed into an arcuate shape corresponding to the shape of the two dimensional detector system 103, and have grooves 505 for the insertion of the collimator plates 504. The grooves 505 are formed at the same pitch along the X ray incident direction such that an X ray focal point exists in a plane including the inserted collimator plates. The upper support 500 and the lower support 501 are fixed side by side with the side surface members 502 so as to make the corresponding grooves 505 face each other.

Figure 4:
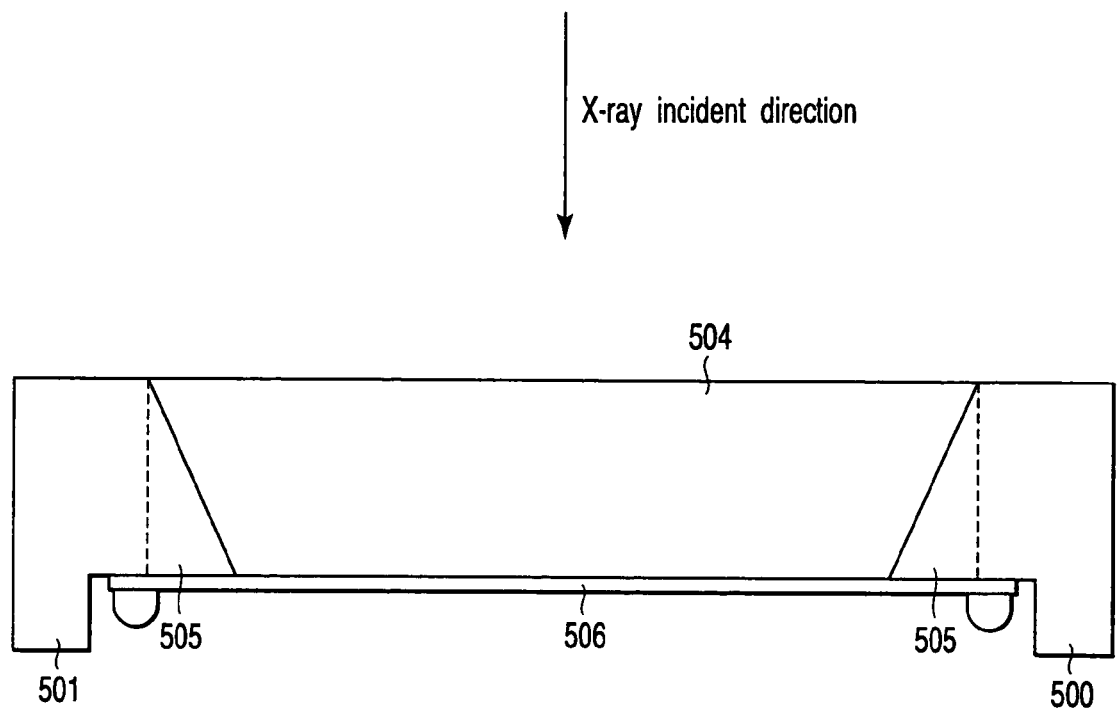
FIG. 4 is a view showing a form of supporting collimator plates 504 by using grooves 505 of upper and lower supports 500 and 501 and an abutment plate 503.

Note that each of the grooves 505, as shown in FIG. 4, is triangular shape in the view of y-direction (channel direction). Each groove is formed in this shape in consideration of convenience in inserting the collimator plate 504 into the groove 505. However, the shape of each groove 505 is not limited to this and may have any shape as long as it can support the collimator plate 504.

The abutment plate 503 is a plate formed into an arcuated shape corresponding to the shape of the two-dimensional detector system 103 (i.e., the shapes of the upper support 500 and lower support 501), and has grooves 506 formed at the same pitch as that of the grooves 505 which the upper support 500 and the lower support 501 have. The abutment plate 503 is made of a material exhibiting high X-ray resistance, processability, X-ray transparency, and mechanical structural strength, e.g., polyethylene terephthalate, an epoxy resin, or a carbon fiber resin. The abutment plate 503 is fixed to the arcuated outside portions of the upper support 500 and lower support 501 (on the outside arcuated side, i.e., the detection surface side of the X-ray detector) such that the grooves 506 correspond to the grooves 505 of the upper support 500 and lower support 501.

The collimator plate 504 is made of a metal exhibiting excellent rigidity, X-ray shielding property, and mechanical structure strength, e.g., tungsten or molybdenum. As shown in FIG. 4, the collimator plates 504 are inserted into the grooves 505 of the upper support 500 and lower support 501 and the grooves 506 of the abutment plate 503, with each being supported at its three sides, and are arranged along a direction almost perpendicular to the slice direction. Note that the collimator plates 504 are fixed in the grooves 505 and 506 with an adhesive.

(Method of Forming Grooves in Abutment Plate)

A method of forming the grooves 506 in the abutment plate 503 will be described next.

Figure 5:
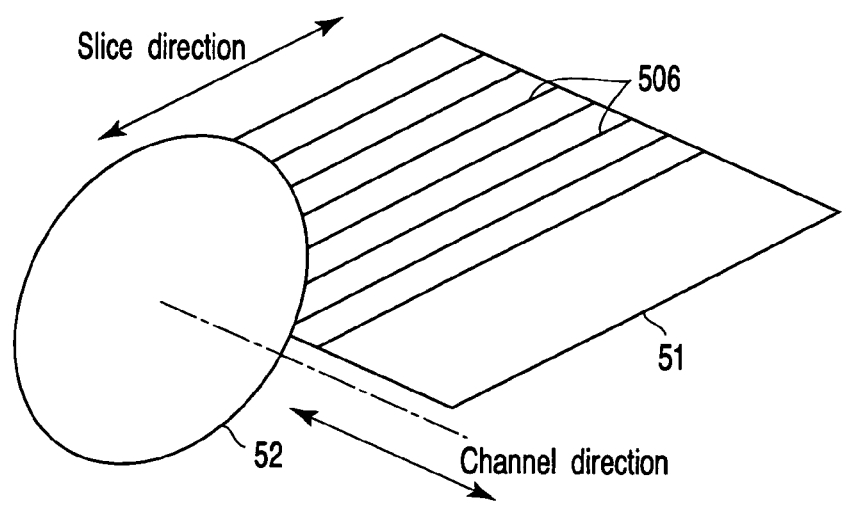
FIG. 5 is a view for explaining a method of forming grooves 506 in the abutment plate 503.

FIG. 5 is a view for explaining the method of forming the grooves 506 in the abutment plate 503. Referring to FIG. 5, first of all, a CFRP plate 51 having the same shape and size as those of the abutment plate 503 (without any groove 506) by using a material exhibiting a high X-ray transmittance such as carbon fiber reinforced plastic (CFRP resin) with a thickness of about 2 to 3 mm.

Figure 6:
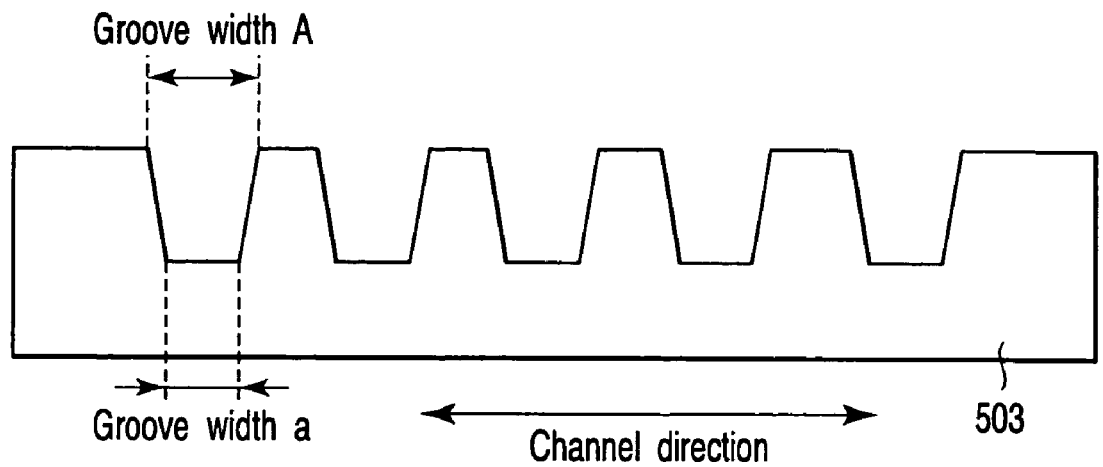
FIG. 6 is a view for explaining the shape of each groove 506 in a manufacturing process for the abutment plate 503.
Figure 7:
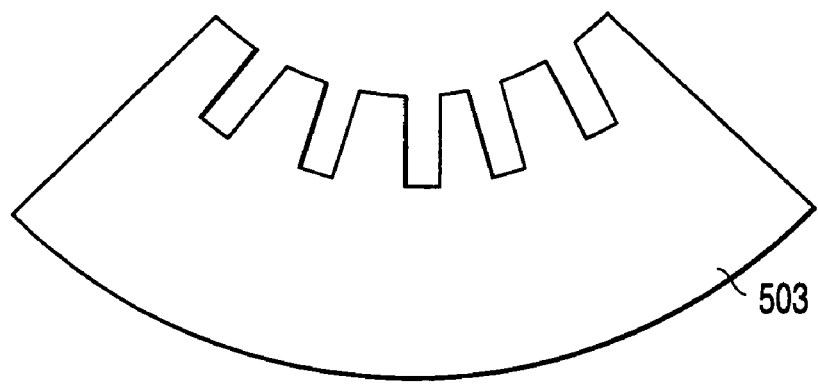
FIG. 7 is a view for explaining the shape of each groove 506 at the time of assembly of the abutment plate 503 to the upper and lower supports 500 and 501.

The grooves 506 are then formed in the CFRP plate 51 along the slice direction by using a blade 52 having a thickness equivalent to the width of the groove 506 in the channel direction. At this time, as shown in FIG. 6, each groove 506 is tapered in the thickness direction of the CFRP plate 51 so as to satisfy A>a where A is the groove width on the insertion side (X-ray tube side) of the collimator plate 504 and a is the groove width on the abutment side (X-ray detector side) of the collimator plate 504. Each groove 506 is formed in such a shape so as to make the groove width A almost equal to the groove width a and set the collimator plate 504 to be almost perpendicular to the abutment plate 503 when the abutment plate 503 is deformed into an arcuated shape to be fixed on the arcuated surfaces of the upper support 500 and lower support 501, as shown in FIG. 7.

In order to make the groove width A almost equal to the groove width a in a state wherein the abutment plate 503 is fixed to the upper support 500 and the lower support 501 (i.e., the state shown in FIG. 7), the value of the groove width A is preferably determined on the basis of the curvature of the abutment plate 503 and the groove width a in the fixed state.

Alternatively, this apparatus may have an arrangement in which each groove 506 is formed to satisfy groove width A>>groove width a (i.e., the groove width A is clearly larger than the groove width a) in the state shown in FIG. 6 so as to satisfy groove width A>groove width a while the abutment plate 503 is fixed to the upper support 500 and lower support 501. With this arrangement, the groove 506 has a tapered shape even in the state wherein the abutment plate 503 is fixed to the upper support 500 and the lower support 501. This makes it easy to insert each collimator plate 504 and makes it possible to realize self-alignment of each collimator plate.

In this embodiment, the abutment plate 503 is formed as an integral part which covers the upper support 500 and the lower support 501 (see FIG. 3). However, the present invention is not limited to this. In consideration of, for example, limitations in terms of groove processing, this apparatus may have a split structure which covers the upper support 500 and the lower support 501 with a plurality of abutment plates. If a split arrangement is to be used, the joint portions are preferably tapered to overlap each other or placed at the shadows of the collimator plates. This makes it possible to avoid the influence of the joint portions.

(Collimator Manufacturing Method)

A method of manufacturing the X-ray detector-side collimator 50 according to the first embodiment will be described next.

Figure 8:
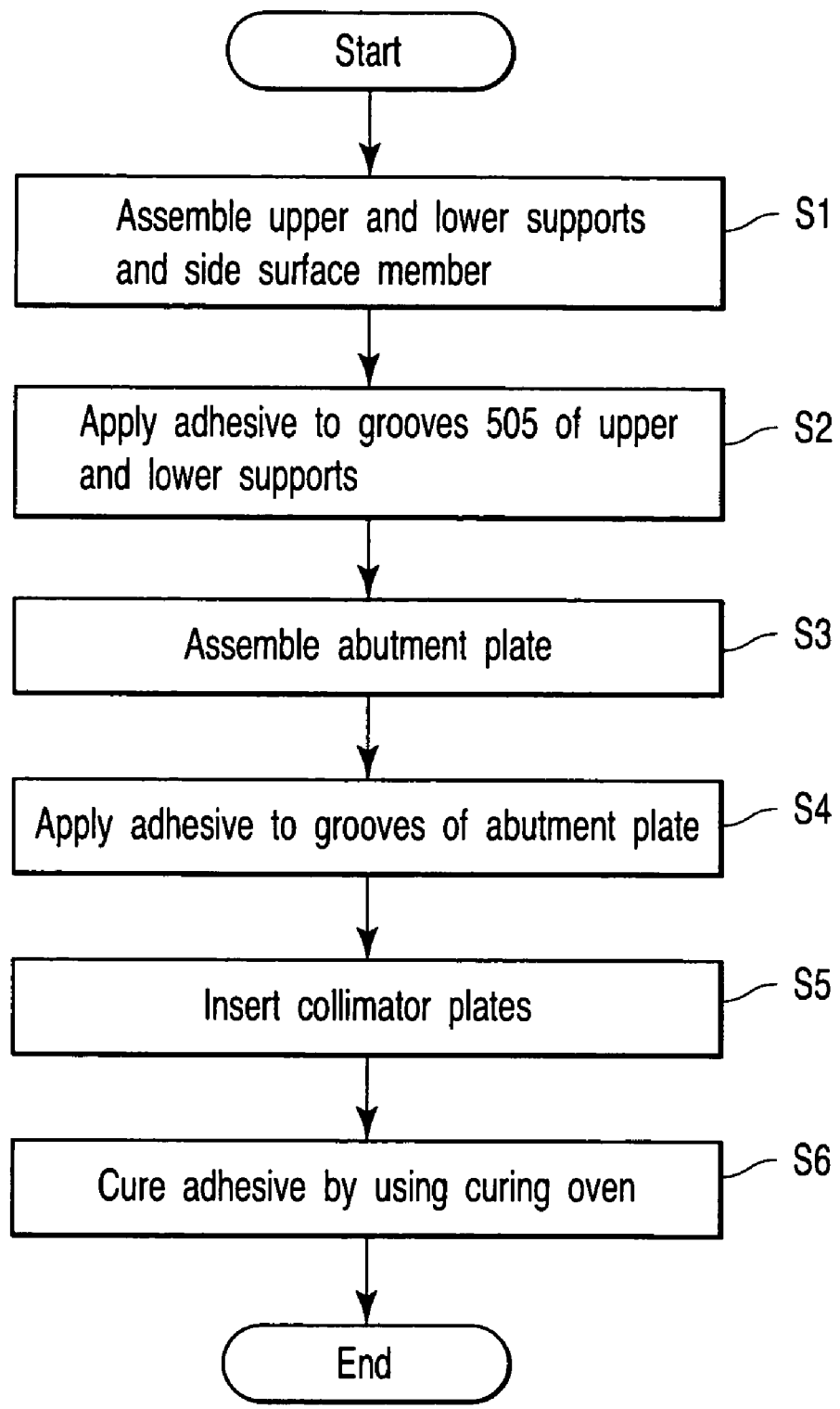
FIG. 8 is a flowchart showing the flow of a manufacturing process for the detector-side collimator 50.

FIG. 8 is a flowchart showing the flow of a manufacturing process for the X-ray detector-side collimator 50. As shown in FIG. 8, first of all, the upper support 500, lower support 501, and side surface member 502 are assembled together to form the outer frame of the X-ray detector-side collimator 50 (step S1).

An adhesive is applied to the grooves 505 formed in the upper support 500 and lower support 501 (step S2). The abutment plate 503 is then elastically deformed into an arcuated shape and fixed to the arcuated side surfaces on the outer periphery sides of the upper support 500 and lower support 501 with screws or the like (step S3).

An adhesive is applied to the grooves 506 of the abutment plate 503 (step S4). The collimator plates 504 are then inserted into the grooves 505 of the upper support 500 and lower support 501 and the grooves 506 of the abutment plate 503 (step S5).

The resultant structure is then placed in a curing oven to cure the adhesive to complete the X-ray detector-side collimator 50 with the three sides of each collimator plate 504 being supported by the grooves 505 and 506 (step S6).

According to the above arrangement, the following effects can be obtained.

This detector-side collimator has an integral structure, and the angle of each collimator plate with respect to the X-ray focal point is determined by the corresponding grooves formed in the upper and lower supports. This prevents the occurrence of deviation of the X-ray focal point among a plurality of modules as in conventional module type collimators, and makes it possible to ensure the continuity of the X-ray focal point. As a consequence, proper X-ray collimation can be realized.

In addition, since this detector-side collimator has an integral structure, no alignment is required between a plurality of models as in conventional module type collimators. This makes it possible to reduce work load in installing and maintaining the X-ray CT apparatus.

Furthermore, this detector-side collimator is configured to support each collimator plate at three sides. Therefore, as compared with a collimator configured to support each collimator plate at two sides, the flatness of each collimator plate can be properly maintained. As a consequence, there is no need to perform maintenance for correcting the warpage of each collimator plate. This makes it possible to reduce the work load and realize proper X-ray collimation in imaging operation for X-ray CT images.

SECOND EMBODIMENT

A detector-side collimator 50 according to the second embodiment of the present invention will be described next. The second embodiment is directed to further ensure the maintenance of the flatness of each collimator plate as compared with the first embodiment.

Figure 9:
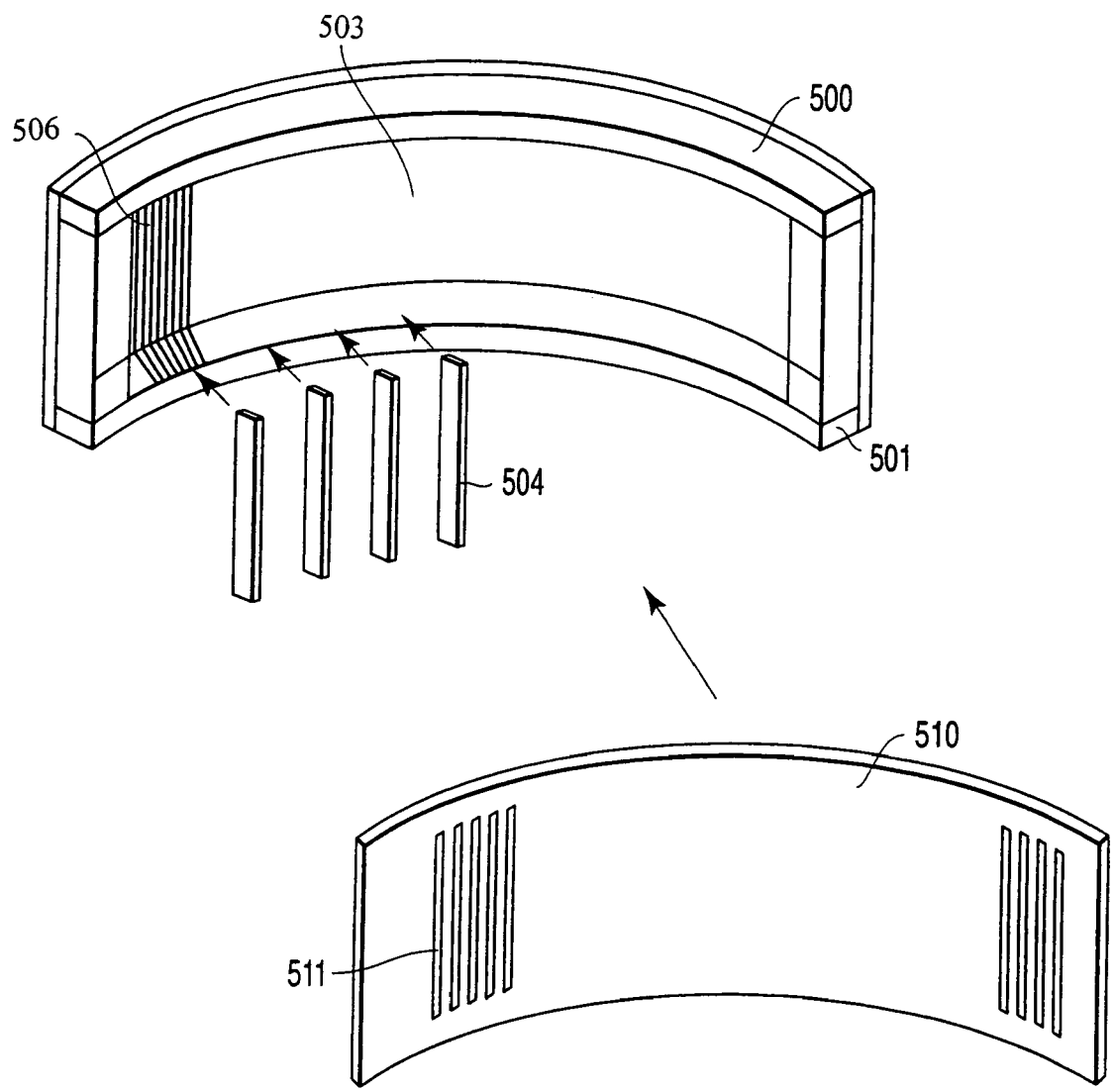
FIG. 9 is a view showing the arrangement of a detector-side collimator 50 according to the second embodiment.

FIG. 9 is a view showing the arrangement of the detector-side collimator 50 which an X-ray CT apparatus 10 according to the second embodiment has. As shown in FIG. 9, the detector-side collimator 50 according to this embodiment further comprises a guide plate 510 on the arcuated side surfaces on the inner periphery side in addition to the arrangement shown in FIG. 3.

The guide plate 510 is a plate formed into an arcuated shape corresponding to the shape of the detector-side collimator 50 (i.e., the shapes of an upper support 500 and lower support 501), and has slits 511 formed at the same pitch as that of grooves 505 and 506. Each slit 511 has a width and height that at least allow a corresponding collimator plate 504 to pass through the slit.

Figure 10A:
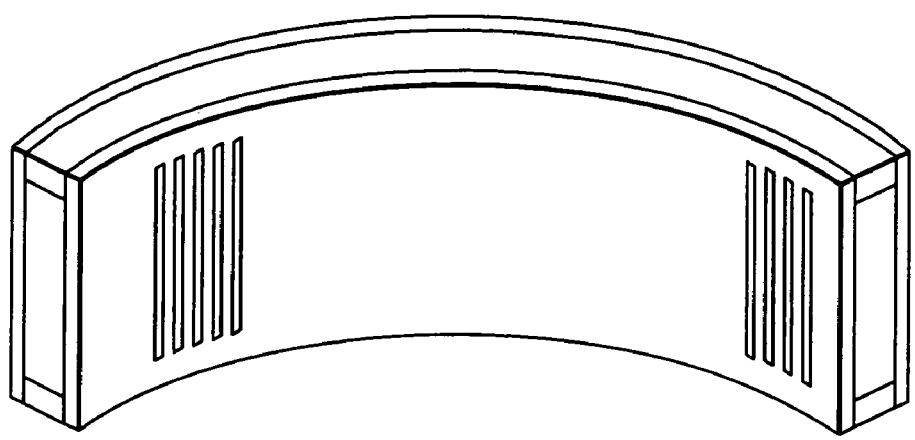
FIG. 10A is a perspective view showing the detector side collimator 50 according to the second embodiment when viewed from the inner arcuate side.

Like the abutment plate 503, the guide plate 510 is made of a material exhibiting high X-ray resistance, processability, X-ray transparency, and mechanical structural strength, e.g., polyethylene terephthalate, an epoxy resin, or a carbon fiber resin. The guide plate 510 is fixed to the arcuated inside portions (inner arcuated sides) of the upper support 500 and lower support 501 such that the slits 511 correspond to the grooves 505 and 506, as shown in FIG. 10A.

Figure 10B:
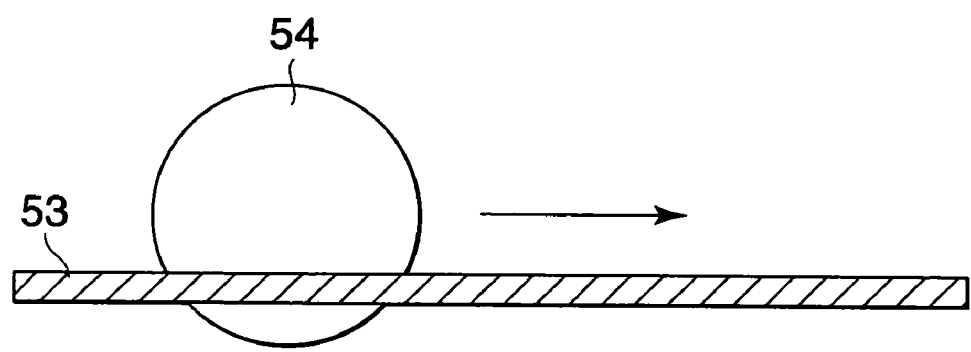
FIG. 10B is a view for explaining a method of manufacturing a guide plate 510.

The guide plate 510 can be manufactured as follows. As shown in FIG. 10B, a CFRP plate 53 having the same shape and size as those of the guide plate 510 (without any slit 511) is formed by using a material having a high X-ray transmittance such as carbon fiber reinforced plastic (CFRP resin).

Figure 10C:
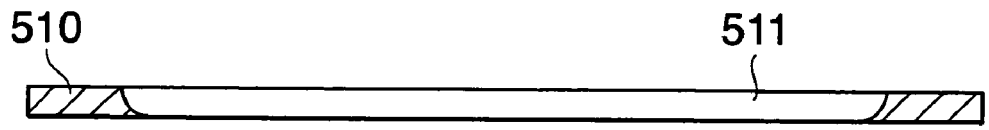
FIG. 10C is a sectional view of the flat guide plate 510 along slits 511.

The slits 511 are then formed in the CFRP plate 53 along the slice direction by using a blade 54 having a thickness equivalent to the width of the slits 511 in the channel direction, thereby manufacturing the guide plate 510. Note that FIG. 10C is a sectional view of the guide plate 510 in a plane along the slits 511.

(Collimator Manufacturing Method)

A method of manufacturing the detector-side collimator 50 according to the second embodiment will be described next.

Figure 11:
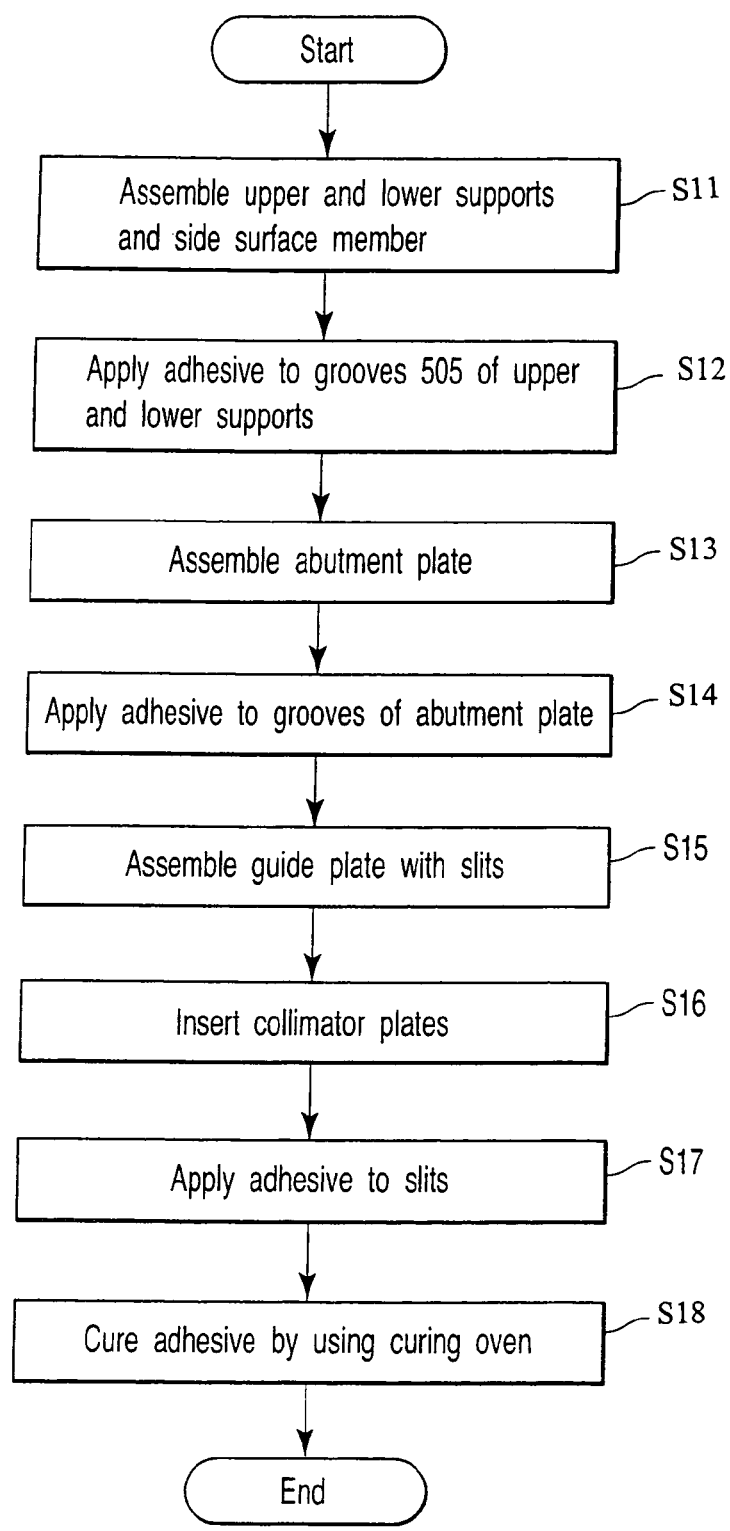
FIG. 11 is a flowchart showing the flow of a manufacturing process for the detector-side collimator 50.

FIG. 11 is a flowchart showing the flow of a manufacturing process for the detector-side collimator 50. The process from steps S11 to S14 in FIG. 11 is the same as the process from steps S1 to S4 shown in FIG. 8, and hence a description thereof will be omitted.

After an adhesive is applied to the grooves 506 of the abutment plate 503, the guide plate 510 with slits is assembled to the upper support 500 and the lower support 501 (step S15). After this assembly, the collimator plates 504 are inserted into the grooves 505 of the upper support 500 and lower support 501 and the grooves 506 of the abutment plate 503 through the slits 511 of the guide plate 510 (step S16).

After an adhesive is applied to the slits 511 (step S17), the resultant structure is placed in a curing oven to cure the adhesive, thereby completing the detector-side collimator 50 with the four sides of each collimator plate 504 being supported by the groove 505, groove 506, and slit 511 (step S18).

According to the above arrangement, in addition to the effects described in the first embodiment, the flatness of each collimator plate can be maintained with higher accuracy. Even if, therefore, the detection range in the slice direction is wider, the flatness of each collimator plate can be properly maintained.

THIRD EMBODIMENT

A detector-side collimator according to the third embodiment of the present invention, and an X-ray CT apparatus comprising such collimator will be described. The present detector-side collimator has a structure in which each collimator plate is supported by four sides, with an upper support, a lower support, an integral abutment plate and an integral internal diameter cover.

Figure 12:
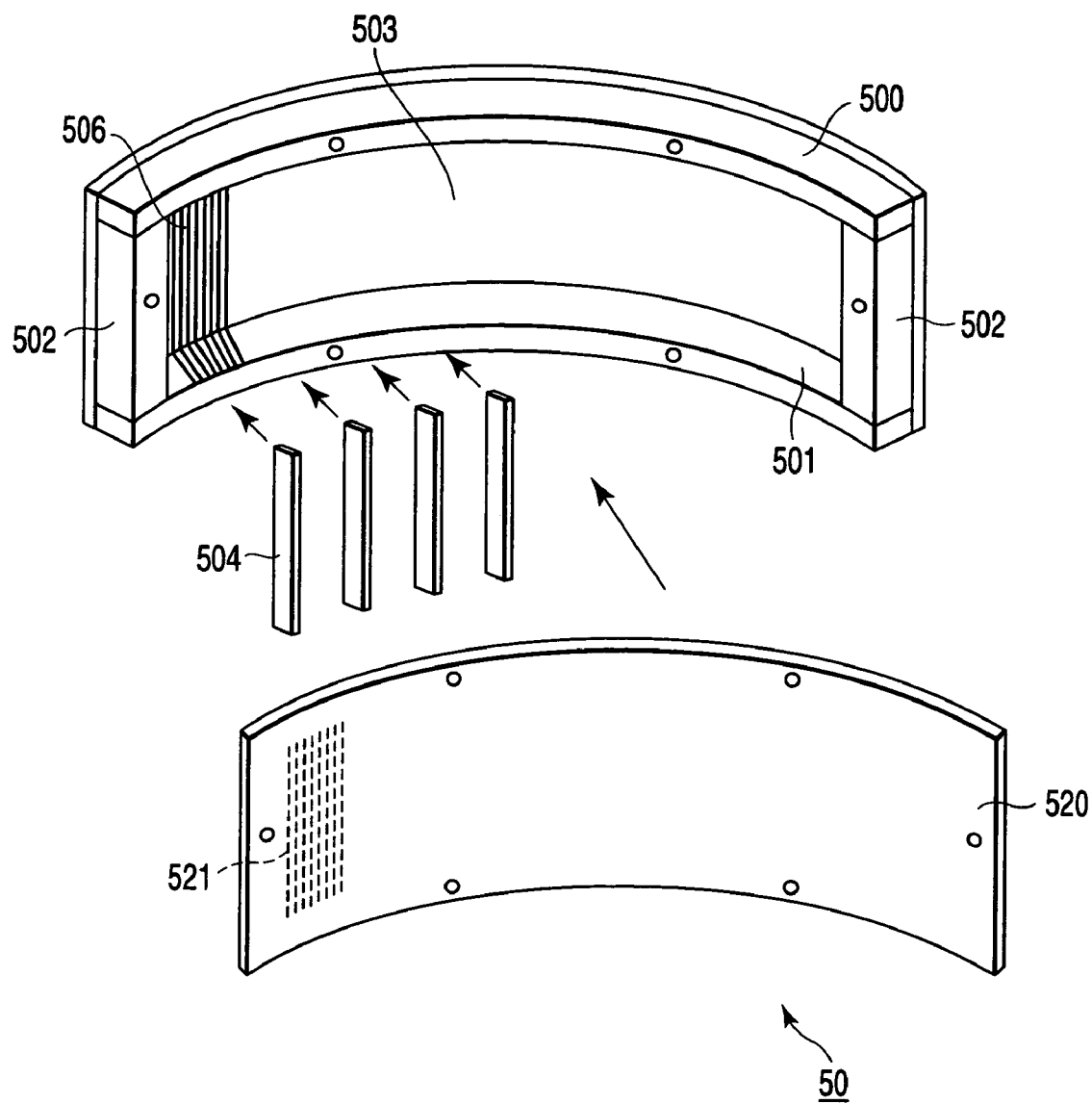
FIG. 12 is a view showing the arrangement of a detector-side collimator 50 possessed by an X-ray CT apparatus 10 according to the third embodiment.

FIG. 12 is a view showing the arrangement of a detector-side collimator 50 possessed by an X-ray CT apparatus 10 according to the third embodiment. As illustrated, the detector-side collimator 50 according to the present embodiment comprises an upper support 500, a lower support 501, side surface members 502, an abutment plate 503, an integral internal diameter cover 520 and a plurality of collimator plates 504.

The abutment plate 503 is in an integral structure and has grooves 506 so as to insert one side of the collimator plate 504.

The internal diameter cover 520 is a plate formed in a shape of the upper support 500 and the lower support 501 (i.e. in an arcuated shape). The internal diameter cover 520 which is a cover to support the collimator plate 504 from the internal diameter-side of the upper support 500 and the lower support 501 has grooves 521 to insert one side of each collimator plate 504. Likewise the abutment plate 503, this internal diameter cover 520 is made of a material exhibiting high X-ray resistance, processability, X-ray transparency, and mechanical structural strength, e.g., polyethylene terephthalate, an epoxy resin, or a carbon fiber resin.

Figure 13:
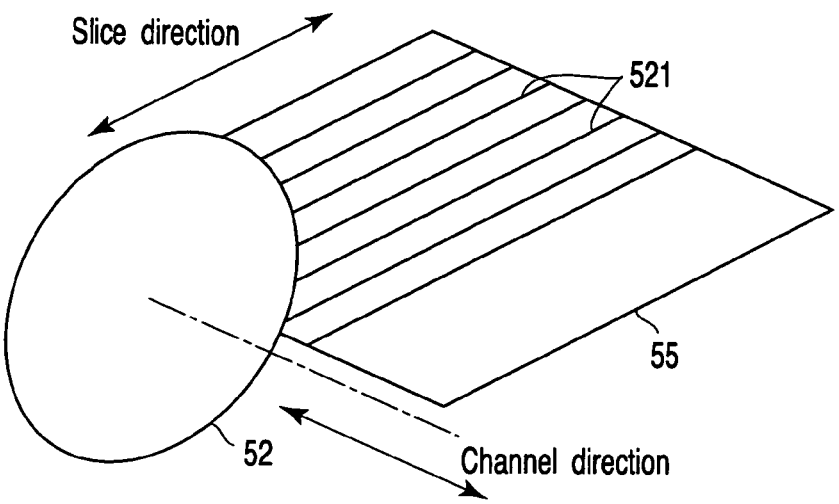
FIG. 13 is a view for explaining a method of forming grooves 521 of internal diameter cover 520.

FIG. 13 is a view for explaining a method of forming grooves 521 of the internal diameter cover 520. As illustrated, first, a CFRP plate 55 bearing the shape and size of the internal diameter cover 520 (without any groove 521) is formed by using a material having a high X-ray transmittance such as carbon fiber reinforced plastic (CFRP resin) in the thickness of about 2 to 3 mm.

Figure 14:
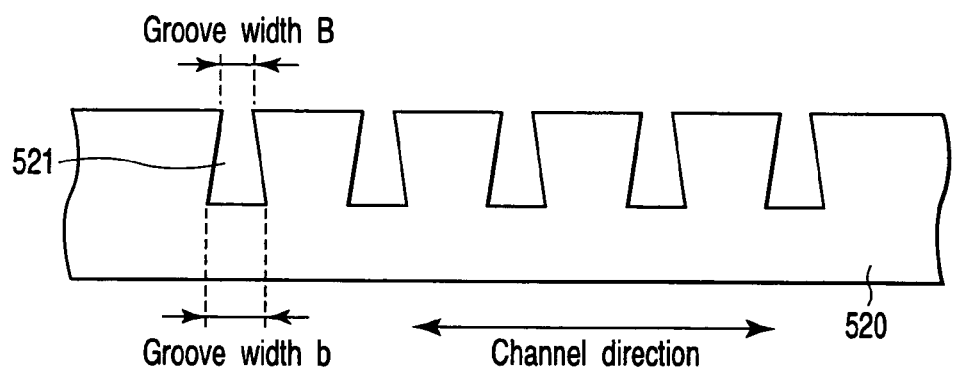
FIG. 14 is a view for explaining a method of forming grooves 521 of internal diameter cover 520.
Figure 15:
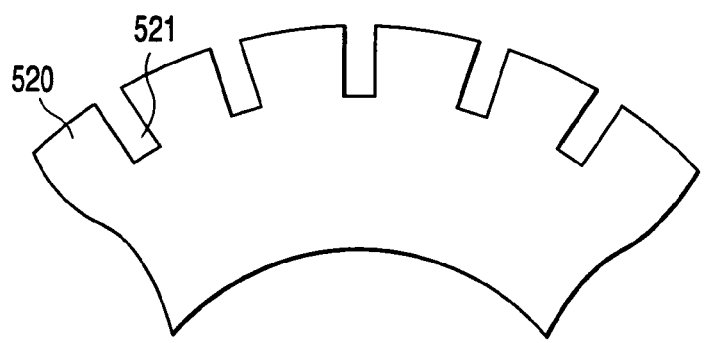
FIG. 15 is a view for explaining a method of forming grooves 521 of internal diameter cover 520.

The grooves 521 are then formed on the CFRP plate 55 along the slice direction by using a blade 52 having a thickness equivalent to the width of the grooves 521 in the channel direction. At this time, as shown in FIG. 14, each groove 521 is tapered in the thickness direction of the CFRP plate 55 so as to satisfy groove widths B>b where B is the groove width on the insertion side (X-ray detector-side) of the collimator plate 504 and b is the groove width on the abutment side (X-ray tube-side) of the collimator plate 504. Each groove 521 is formed in such a shape so as to make the groove width B almost equal to the groove width b and set the collimator plate 504 almost perpendicular to the internal diameter cover 520 when deforming the internal diameter cover 520 into an arcuated shape to be fixed along the arcuated surfaces of the upper support 500 and lower support 501, as shown in FIG. 15.

In order to make the groove width B almost equal to the groove width b in a state where the internal diameter cover 520 is fixed to the upper support 500 and the lower support 501 (i.e., the state shown in FIG. 15), the value of the groove width B is preferably determined on the basis of the curvature of the internal diameter cover 520 and the groove width b in such fixed state.

(Collimator Manufacturing Method)

A method of manufacturing the detector-side collimator 50 according to the present embodiment will be described next.

Figure 16:
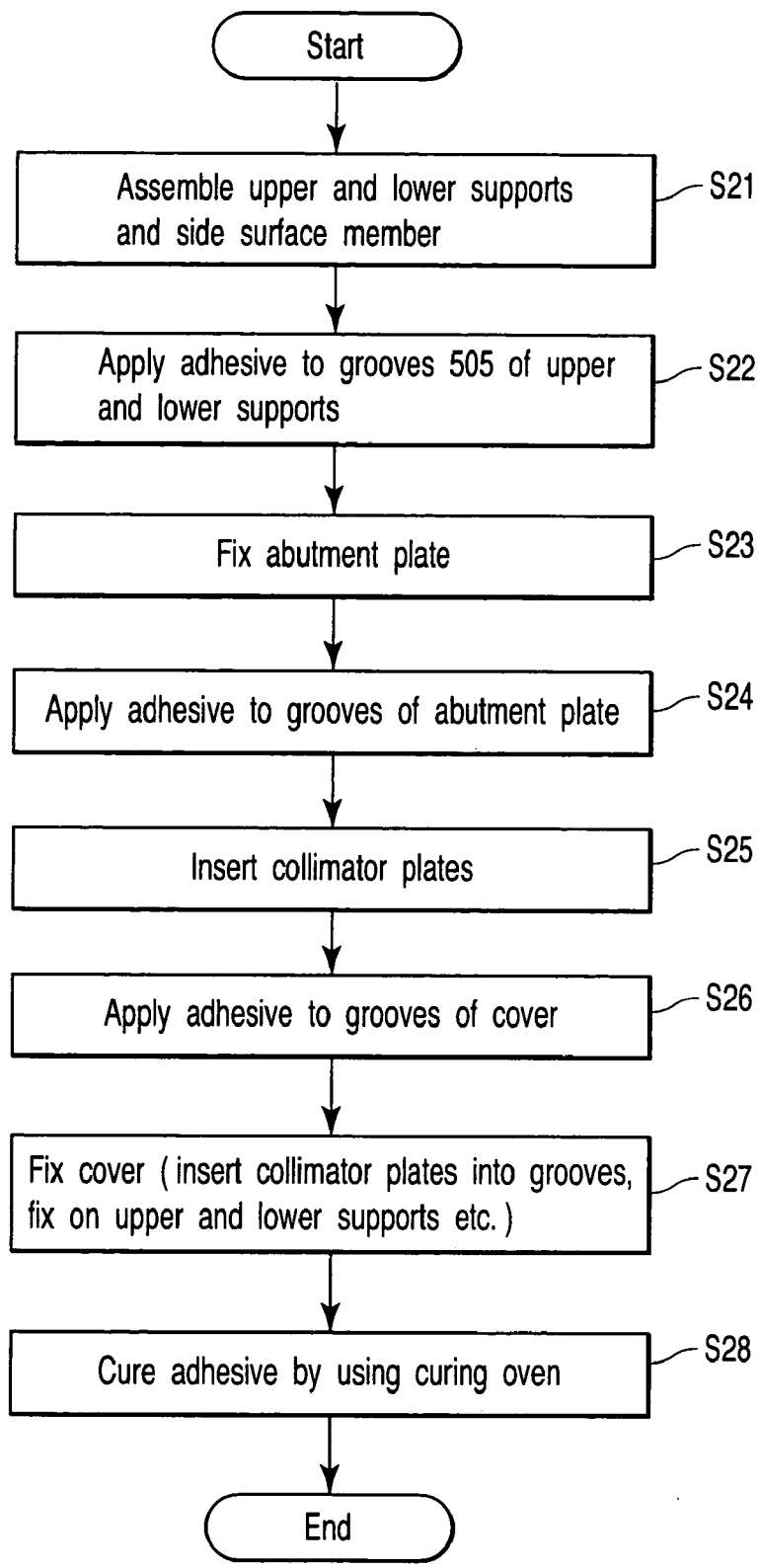
FIG. 16 is a flow chart showing the flow of a manufacturing process for the detector-side collimator 50 according to the third embodiment.

FIG. 16 is a flowchart showing the flow of a manufacturing process for the detector-side collimator 50. The process from steps S21 to S24 in FIG. 16 is approximately the same as the process from steps S1 to S4 shown in FIG. 8, and hence a description thereof will be omitted.

After an adhesive is applied to grooves 506 of the abutment plate 503, the collimator plates 504 are inserted in grooves 505 of the upper support 500 and the lower support 501 and the grooves 506 of the abutment plate 503 (step S25).

Then, after an adhesive is applied to the grooves 521 of the internal diameter cover 520 (step S26), the internal diameter cover 520 is fixed on the upper support 500, the lower support 501, and the side surface members 502 while inserting each collimator plate 504 into each groove 521, (step S27). In addition, when inserting each collimator plate 504 into each groove 521, the internal diameter cover 520 may also be pressed along the inserting direction, or may be pressed while causing either one of the collimator plate 504-side and the internal diameter cover 520 to vibrate, if needed.

The collimator 50 is then placed in a curing oven to cure the adhesive (step S28). As a result of each process above, the detector-side collimator 50 in which the four sides of each collimator plate 504 are supported by the grooves 505, 506 and 521 is completed.

Further, the adhesive for grooves 505, 506 and 521 is not mandatory. For example, if each collimator plate 504 can be supported sufficiently without an adhesive, it is fine to omit the application of adhesives on at least one or all grooves. The same applies to other embodiments in this regard.

MODIFIED EXAMPLES

Next, modified examples of the present embodiment will be explained. A detector-side collimator 50 according to the present modified example supports one side among the four sides of a collimator signal plate 504 by an internal diameter cover which does not have groove 521.

Figure 17:
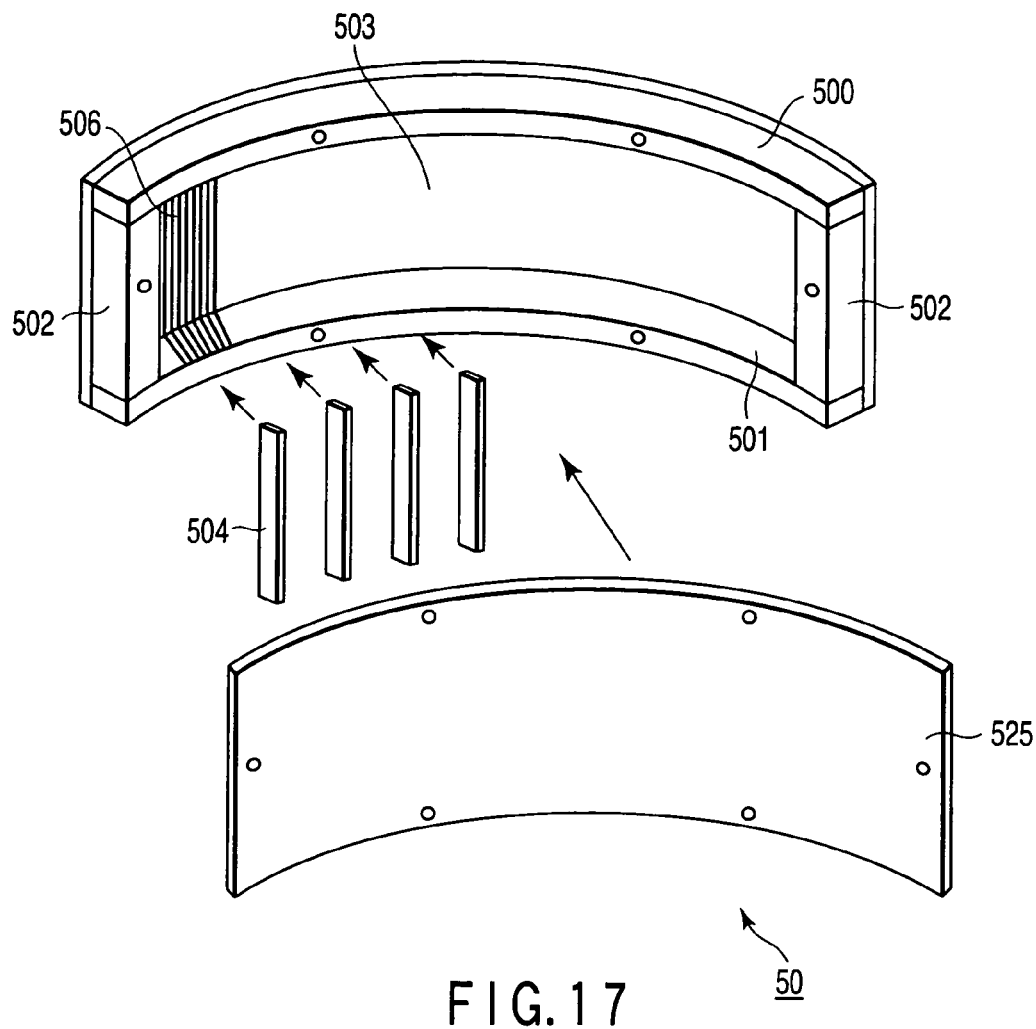
FIG. 17 is a view showing the arrangement of the detector-side collimator 50 according to a modified example of the third embodiment.

FIG. 17 is a view showing the arrangement of a detector-side collimator 50 according to the present modified example. As illustrated, the detector-side collimator 50 is provided with an internal diameter cover 525, which is integral and does not have grooves for inserting the collimator plates 504.

Figure 18:
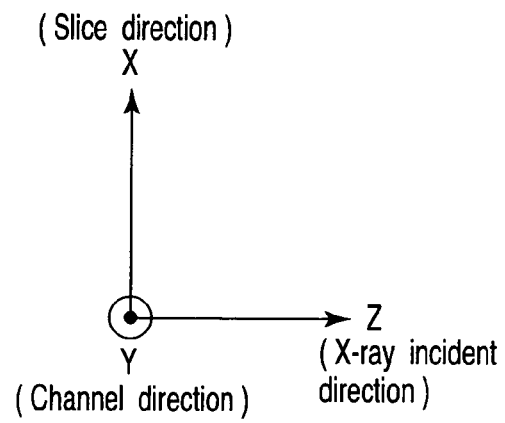
FIG. 18 is a view showing the arrangement of the detector-side collimator 50 according to a modified example of the third embodiment.
Figure 18:
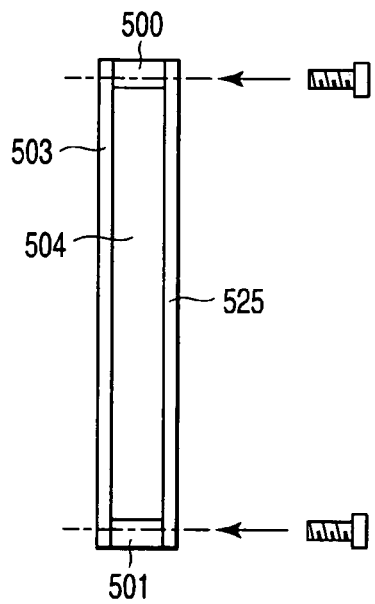

Except for the point that there is no groove 521 formed on the internal diameter cover 525, it has the same structure as the internal diameter cover 520. As shown in FIG. 18, this internal diameter cover 525 is fixed on the upper support 500, lower support 501 and side surface members 502 in a manner that would press one side of each collimator plate 504 (i.e., one side of the X-ray tube 101-side). Pressed by the internal diameter cover 525, the collimator plate 504 is supported by one side.

(Collimator Manufacturing Method)

A method of manufacturing the detector-side collimator 50 according to the present modified example will be described next.

Figure 19:
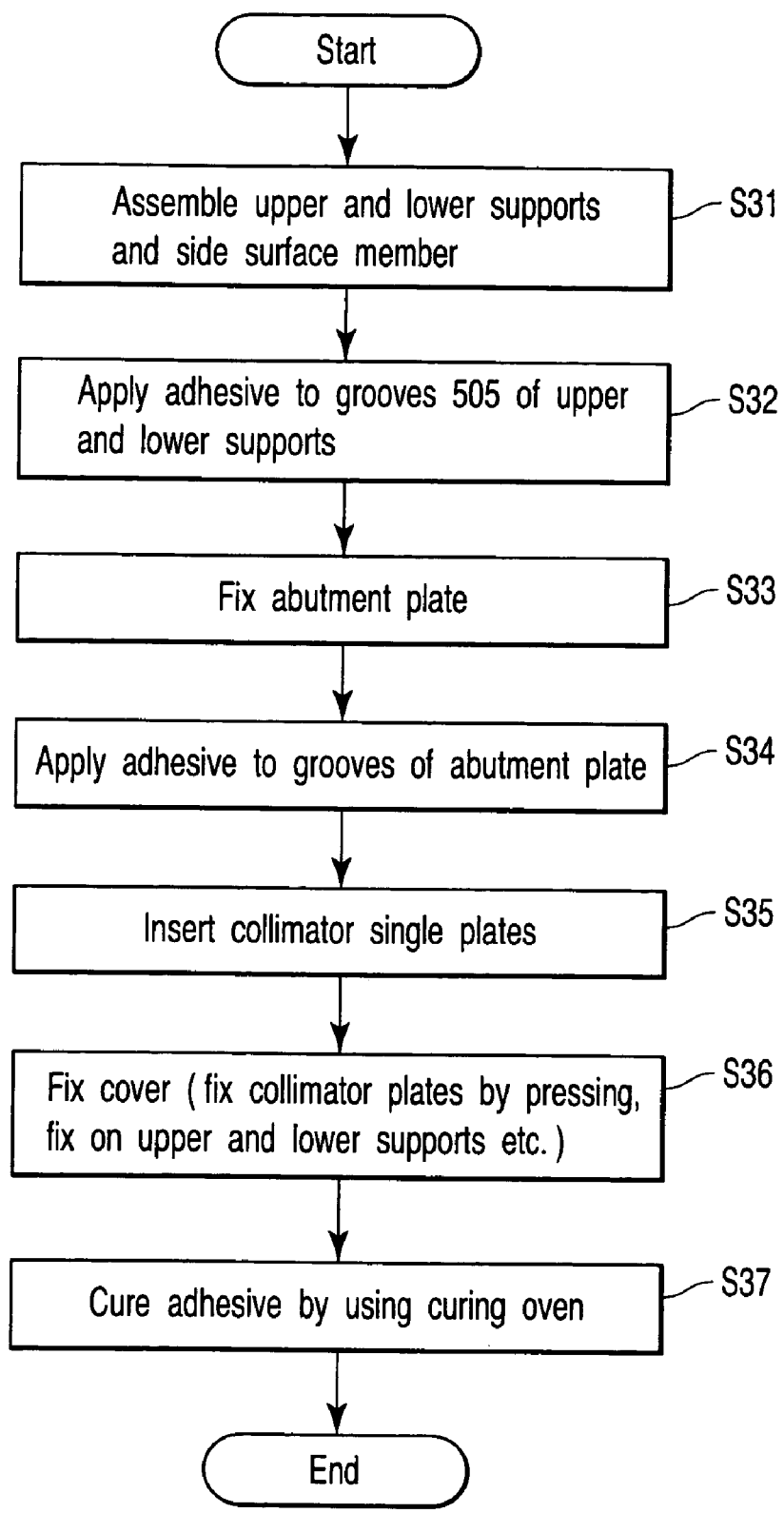
FIG. 19 is a flow chart showing the flow of a manufacturing process for the detector-side collimator 50 according to a modified example of the third embodiment.

FIG. 19 is a flowchart showing the flow of a manufacturing process for the detector-side collimator 50. The process from steps S31 to S35 shown in FIG. 19 is basically the same as the process from steps S21 to S25 shown in FIG. 16, and hence a description thereof will be omitted.

After inserting the collimator plates 504, the internal diameter cover 525 is fixed on the upper support 500, lower support 501 and side surface members 502 in a manner that would press one side of the X-ray tube 101-side of each collimator plate 504 (step S36).

The collimator 50 is then placed in a curing oven to cure the adhesive (step S37). As a result of each process above, the detector-side collimator 50 in which the four sides of each collimator plate 504 are supported by the grooves 505 and 506 and the internal diameter 525 is completed.

According to the above arrangement, in addition to the effects described in the first embodiment, a next new effect can be realized.

In the present detector-side collimator, each collimator plate is supported by four sides. Accordingly, in comparison to the case of the conventional two sides support and the three sides support, it is possible to realize a detector-side collimator with high flatness in the collimator plates. As a result, it is possible to realize an ideal collimation. Particularly, even if the detection range in the slice direction is wider, the flatness of each collimator plate can be properly maintained.

Further, as the collimator plates are supported equally by four sides. For this reason, the collimator plates can maintain high rigidity even when the detector side collimator is rotated with a central focus on the body axis of a subject at a high speed of one second or less per rotation. As a result, the operation of restoring flatness of the collimator plates upon maintenance can be reduced.

FOURTH EMBODIMENT

A detector-side collimator according to the fourth embodiment of the present invention, and an X-ray CT apparatus comprising such collimator will be described. The present detector-side collimator has a structure in which each collimator plate is supported by four sides, with an upper support, a lower support, an integral abutment plate and a module type internal diameter cover.

FIG. 20A is a view showing the arrangement of a detector-side collimator 50 possessed by an X-ray CT apparatus 10 according to the fourth embodiment. As illustrated, the detector-side collimator 50 according to the present embodiment comprises an upper support 500, a lower support 501, side surface members 502, an abutment plate 503, a module type internal diameter cover 530 and a plurality of collimator plates 504.

The abutment plate 503 is in an integral structure and has grooves 506 so as to insert one side of the collimator plate 504.

The internal diameter cover 530 is a plate bearing an arcuated shape corresponding to the curvature (i.e., the curvature of an arc) of the upper support 500 and the lower support 501 in the channel direction, and is arranged plurally along the channel direction. The internal diameter cover 530 is a cover that supports the collimator plate 504 from the internal diameter-side of the upper support 500 and the lower support 501, and has a groove 531 for inserting one side of the collimator plate 504. Likewise the abutment plate 503, this internal diameter cover 530 is made of a material exhibiting high X-ray resistance, processability, X-ray transparency, and mechanical structural strength, such as polyethylene terephthalate, an epoxy resin, or a carbon fiber resin.

Figure 20B:
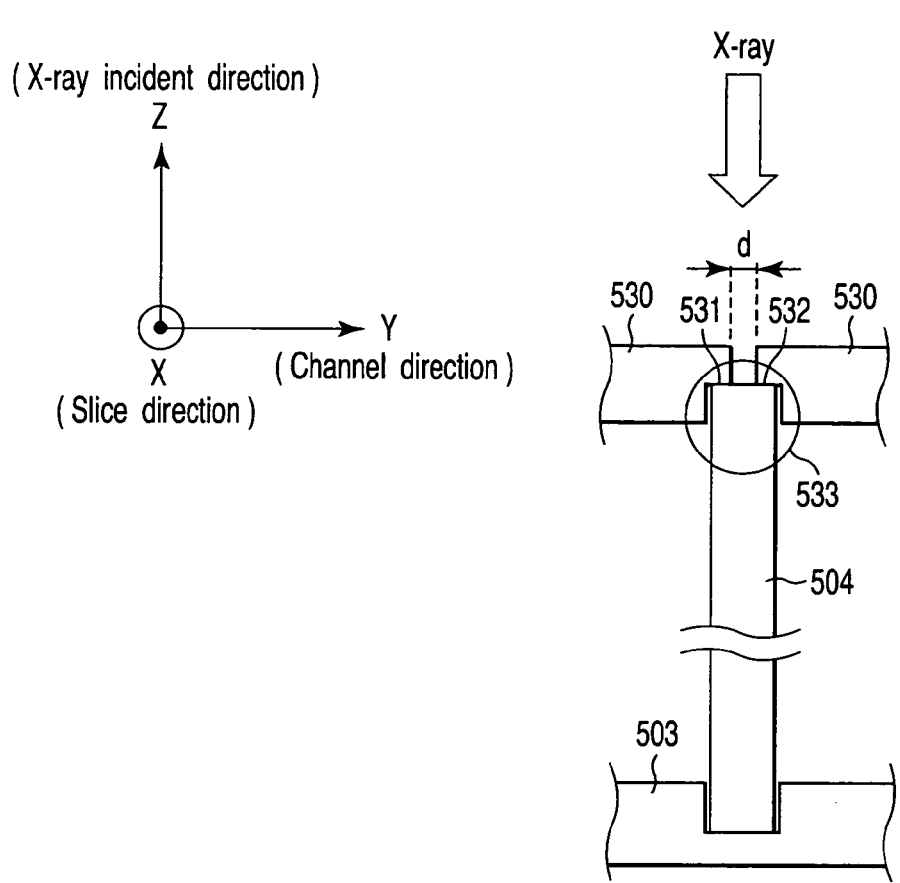
FIG. 20B is a view showing the arrangement of the detector-side collimator 50 possessed by the X-ray CT apparatus 10 according to the fourth embodiment.
Figure 20C:
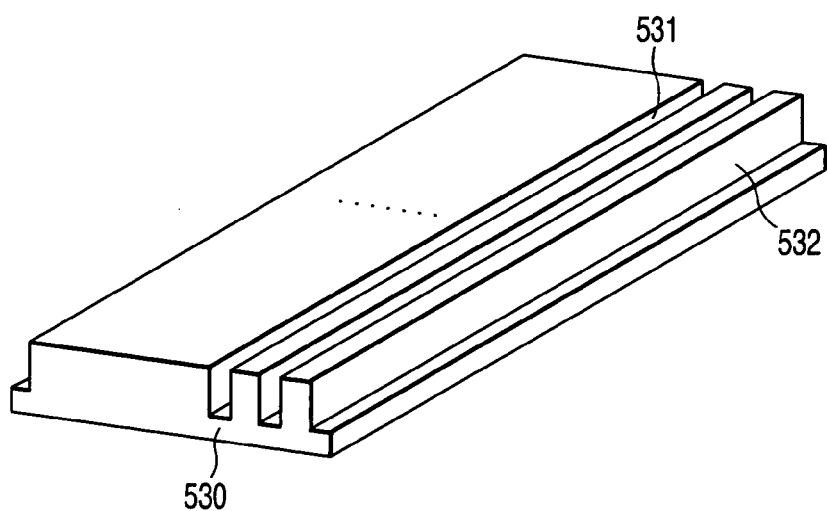
FIG. 20C is a view showing the arrangement of the detector-side collimator 50 possessed by the X-ray CT apparatus 10 according to the fourth embodiment.

Further, the internal diameter cover 530 has groove 532, which is different from groove 531. When arranging a plurality of internal diameter covers 530 along the channel direction, the grooves 532 of the neighboring internal diameter covers 530 form a groove 531 for inserting the collimator plate 504 as shown in FIG. 20B and 20C. By inserting the collimator plates 504 in the grooves 531 formed by the grooves 532 of the neighboring internal diameter covers 530 in this manner, an effect on the X-ray detection caused by the joint of the internal diameter cover 530 can be circumvented.

Figure 20D:
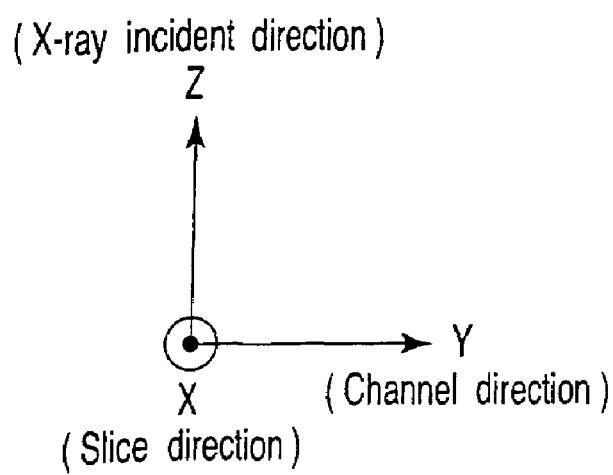
FIG. 20D is a view showing a modified example of the detector-side collimator 50 (detail description of the joint part between the neighboring internal diameter covers 530) according to the fourth embodiment.
Figure 20D:
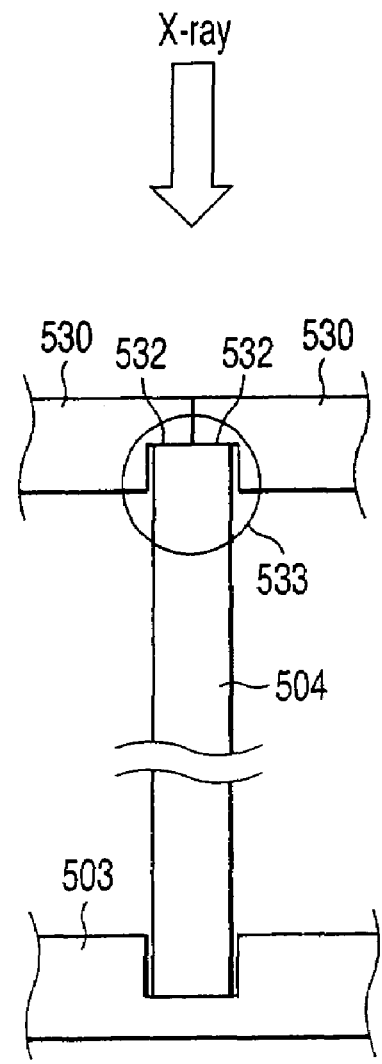

In addition, the internal diameter cover 530 can be arranged either in the channel direction with a certain space d as in FIG. 20B or in the channel direction that enables the neighbors to come in contact as in FIG. 20D. In either arrangement, the width of groove 532 in the channel direction is designed to form a groove 533 by the grooves 532 of the neighboring internal diameter covers 530.

Such internal diameter cover 530 can be produced by the means almost similar to the internal diameter cover 520 according to the third embodiment.

(Collimator Manufacturing Method)

A method of manufacturing the detector-side collimator 50 according to the present embodiment will be described next.

Figure 21:
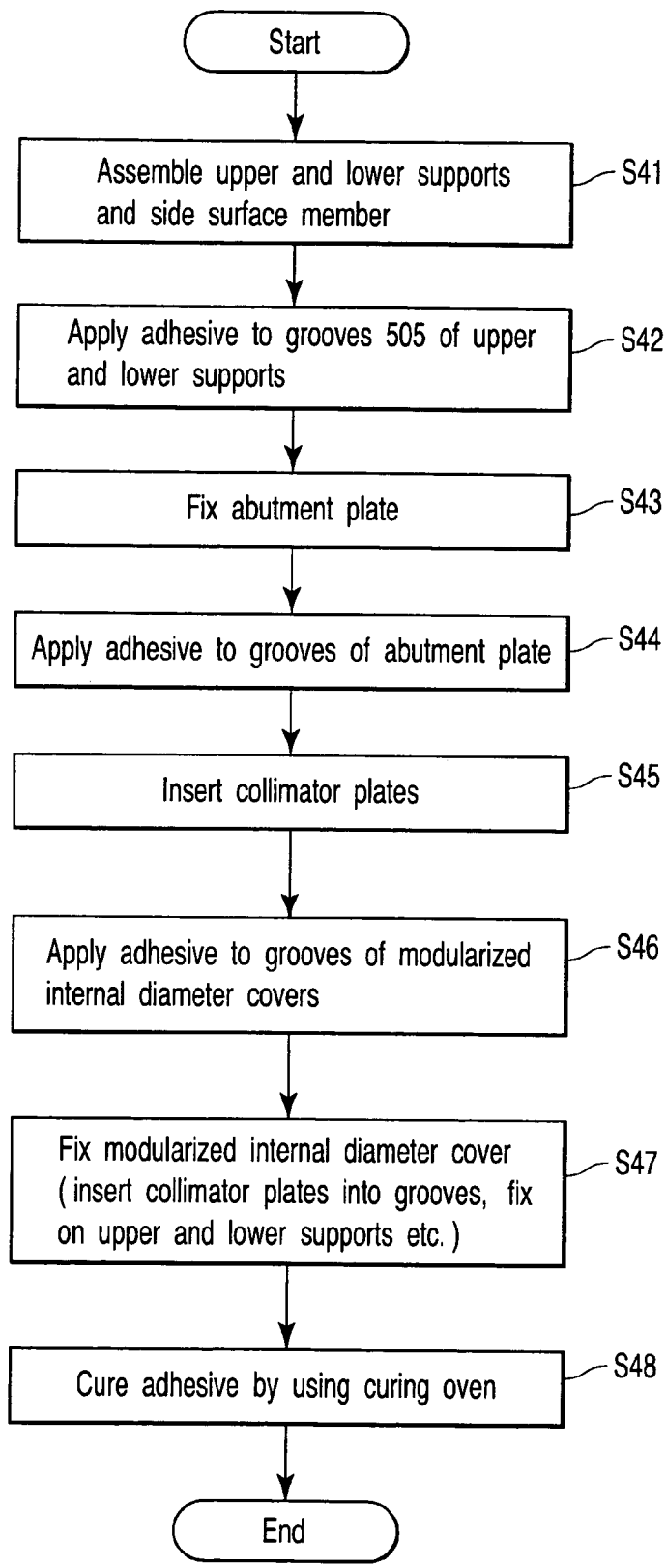
FIG. 21 is a flow chart showing the flow of a manufacturing process for the detector-side collimator 50 according to the fourth embodiment.

FIG. 21 is a flowchart showing the flow of a manufacturing process for the detector-side collimator 50. The process from steps S41 to S45 shown in FIG. 21 is basically the same as the process from steps S31 to S35 shown in FIG. 19, and hence a description thereof will be omitted.

After inserting the collimator plates 504, an adhesive is applied to the grooves 531 and the grooves 532 of each modularized internal diameter cover 530 (step S46), which is then fixed on the upper support 500, lower support 501 and side surface members 502 while inserting each collimator plate 504 in each groove 531 (step S47). Meanwhile, when inserting each collimator plate 504 in each groove 531 and groove 532, the internal diameter cover 530 may be pressed along the inserting direction, or may be pressed while causing at least either one of the collimator plate 504-side and the internal diameter cover 530 to vibrate, according to need.

The collimator 50 is then placed in a curing oven to cure the adhesive (step S48). As a result of each process above, the detector-side collimator 50 in which the four sides of each collimator plate 504 is being supported by the grooves 505, 506 and 521 is completed.

MODIFIED EXAMPLE

Next, modified examples of the present embodiment will be explained. A detector-side collimator 50 according to the present modified example supports one side among the four sides of a collimator signal plate 504 by a modularized internal diameter cover, which does not have grooves 532.

FIG. 22 is a view showing the arrangement of the detector-side collimator 50 according to the present modified example. As illustrated, the detector-side collimator 50 comprises an internal diameter cover 533, which is modularized and does not have grooves for inserting collimator plates 504.

Except for the point that there is no groove 531 formed on the internal diameter cover 533, it has the same arrangement as the internal diameter cover 530. Likewise the example shown in FIG. 18, each internal diameter cover 533 is fixed on the upper support 500, lower support 501 and side surface members 502 in a manner that presses one side of each collimator plate 504 (i.e., one side of the X-ray tube 101-side). Pressed by the internal diameter cover 533, the collimator plate 504 is supported by one side.

(Collimator Manufacturing Method)

A method of manufacturing the detector-side collimator 50 according to the present modified example will be described next.

Figure 23:
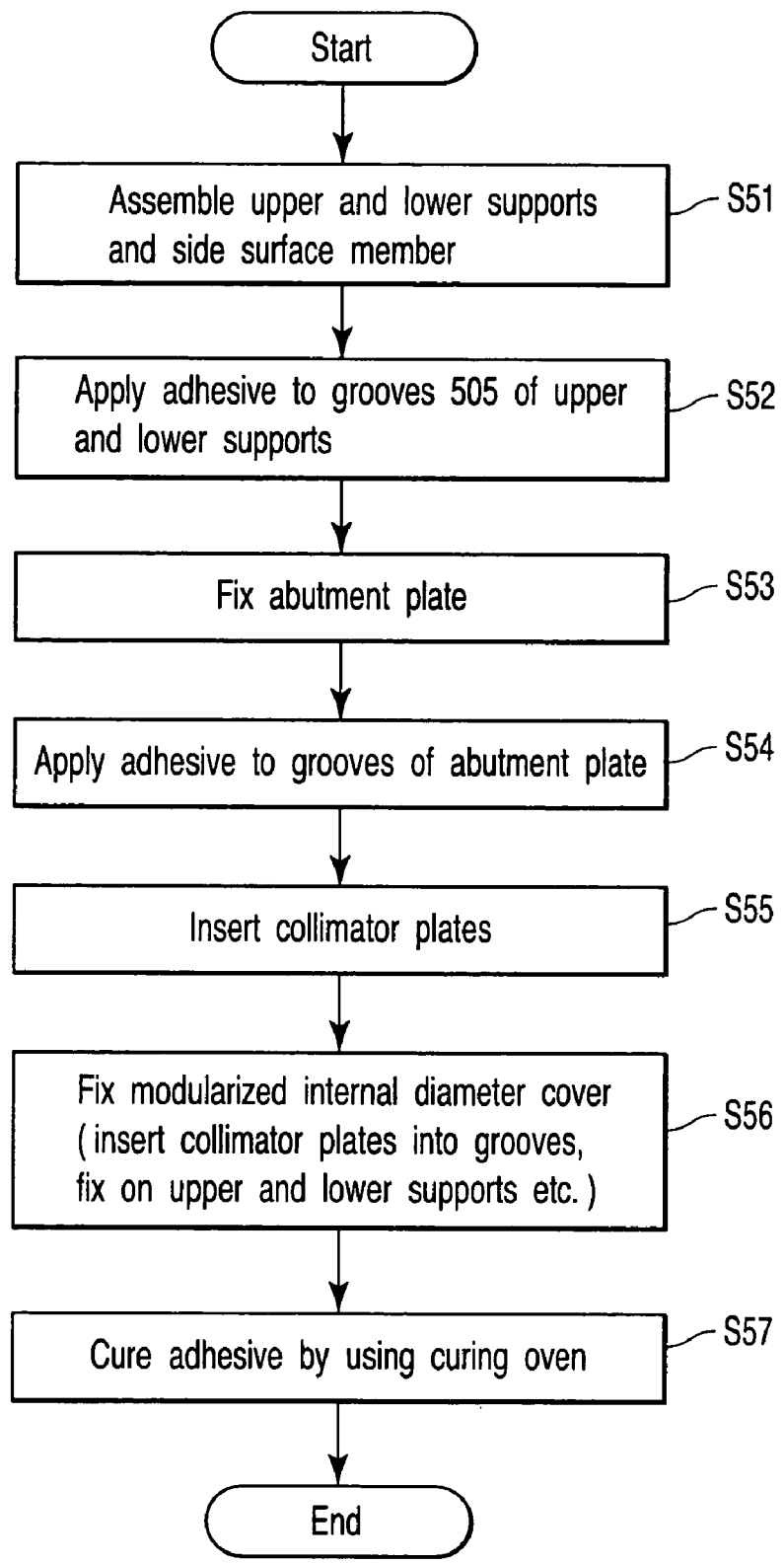
FIG. 23 is a flow chart showing the flow of a manufacturing process for the detector-side collimator 50 according to a modified example of the fourth embodiment.

FIG. 23 is a flowchart showing the flow of a manufacturing process for the detector-side collimator 50. Since the process from steps S51 to S55 is basically the same as the process from steps S41 to S45 shown in FIG. 21, description thereof will be omitted.

After inserting the collimator plates 504, the internal diameter cover 533 is fixed on the upper support 500, lower support 501 and side surface members 502 in a manner that presses one side of the X-ray tube 101-side of each collimator plate 504 (step S56).

The collimator 50 is then placed in a curing oven to cure the adhesive (step S57). As a result of each process above, the detector-side collimator 50 in which the four sides of each collimator plate 504 is being supported by the grooves 505 and 506 and the internal diameter cover 533 is completed.

According to the above arrangement, the next new effect can be realized in addition to the effect described in the third embodiment. In other words, being modularized, the internal diameter cover supporting one side of the collimator plate can be partially disassembled. Accordingly, when there is need to, for example, adjust or change a portion of the collimator plate, this may be done by simply removing the internal diameter cover supporting such collimator plate. Consequently, this can reduce operation loads and expenses upon maintenance.

FIFTH EMBODIMENT

A detector-side collimator according to the fifth embodiment of the present invention, and an X-ray CT apparatus comprising such collimator will be described. The present detector-side collimator has a structure in which each collimator plate is supported by four sides, with an upper support, a lower support, an integral internal diameter cover and a module type abutment plate.

Figure 24:
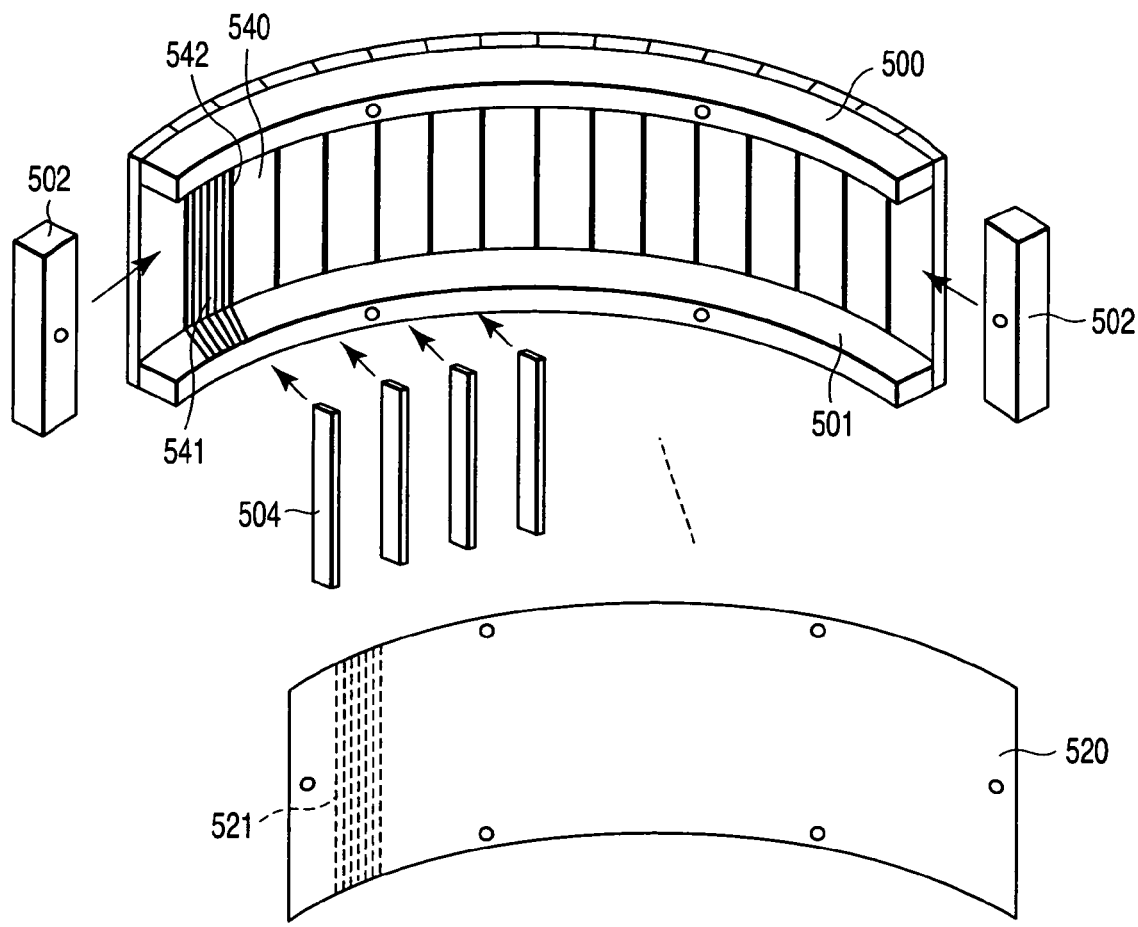
FIG. 24 is a view showing the arrangement of the detector-side collimator 50 possessed by the X-ray CT apparatus 10 according to a fifth embodiment.

FIG. 24 is a view showing the arrangement of a detector-side collimator 50 possessed by an X-ray CT apparatus 10 according to the fifth embodiment. As illustrated, the detector-side collimator 50 according to the present embodiment comprises an upper support 500, a lower support 501, side surface members 502, a modularized abutment plate 540, an integral internal diameter cover 520 and a plurality of collimator plates 504.

Figure 25:
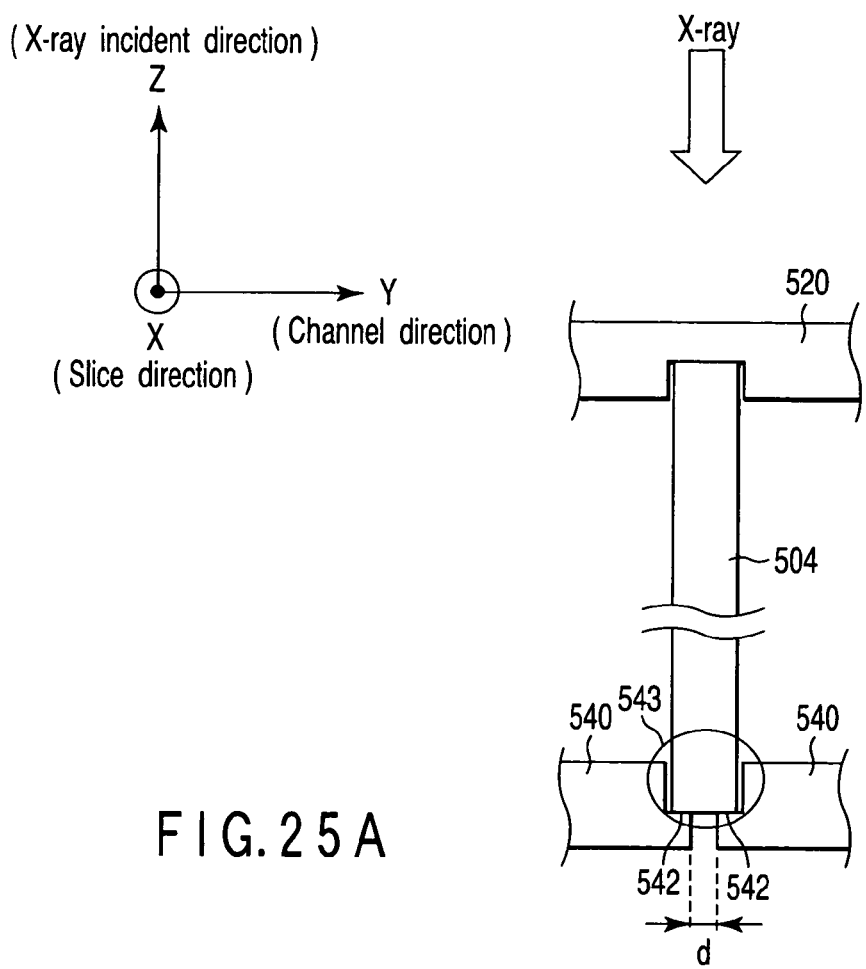
FIG. 25A is a view showing an aspect of an abutment plate 540 of the detector-side collimator 50 according to the fifth embodiment.
FIG. 25B is a view showing an aspect of an abutment plate 540 of the detector-side collimator 50 according to the fifth embodiment.
FIG. 25C is a view showing an aspect of an abutment plate 540 of the detector-side collimator 50 according to the fifth embodiment.
Figure 25:
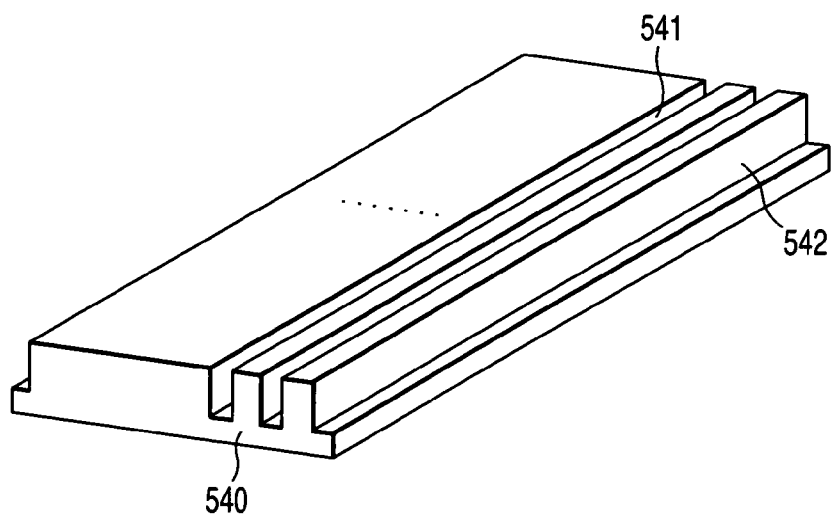

FIG. 25A is a view showing an aspect of an abutment plate 540. As illustrated, a plurality of abutment plates 540 is arranged along the channel direction. The abutment plate 540 has a groove 541 to insert one side of the collimator plate 504. Likewise the abutment plate 503, this abutment plate 540 is made of a material exhibiting high X-ray resistance, processability, X-ray transparency, and mechanical structural strength, e.g., polyethylene terephthalate, an epoxy resin, or a carbon fiber resin. Again, the abutment plate 540 can be made by almost the same method as for the abutment plate 503 (see FIGS. 13, 14 and 15).

Further, the abutment plate 540 has a groove 542, which is different from the groove 541. As illustrated in FIGS. 25A and 25B, when arranging a plurality of abutment plates 540 in a channel direction, the grooves 542 of the neighboring abutment plates 540 form a groove 543 for inserting the collimator plate 504. By inserting the collimator plates 504 in the grooves 543 formed by the grooves 542 of the neighboring abutment plates 540 in this manner, an effect on the X-ray detection caused by the joint of the abutment plate 540 can be circumvented.

Figure 25C:
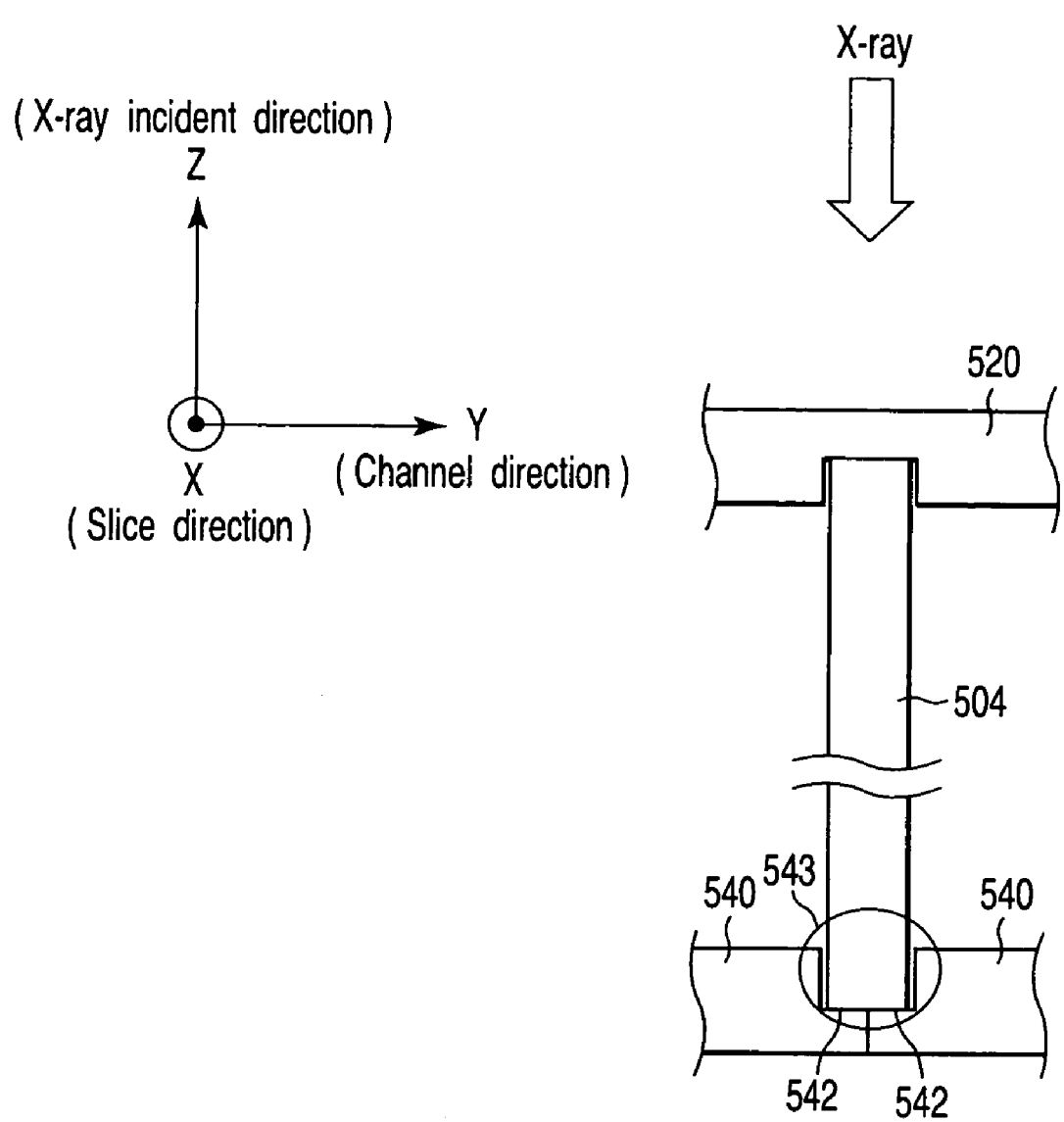

In addition, the abutment plate 540 can be arranged either in the channel direction with a certain space d as in FIG. 25A or in the channel direction which the neighbors come in contact as in FIG. 25C. In either arrangement, the width of the groove 542 in the channel direction is designed to form a groove 543 by the grooves 542 of the neighboring abutment plates 540.

(Collimator Manufacturing Method)

A method of manufacturing the detector-side collimator 50 according to the present embodiment will be described next.

Figure 26:
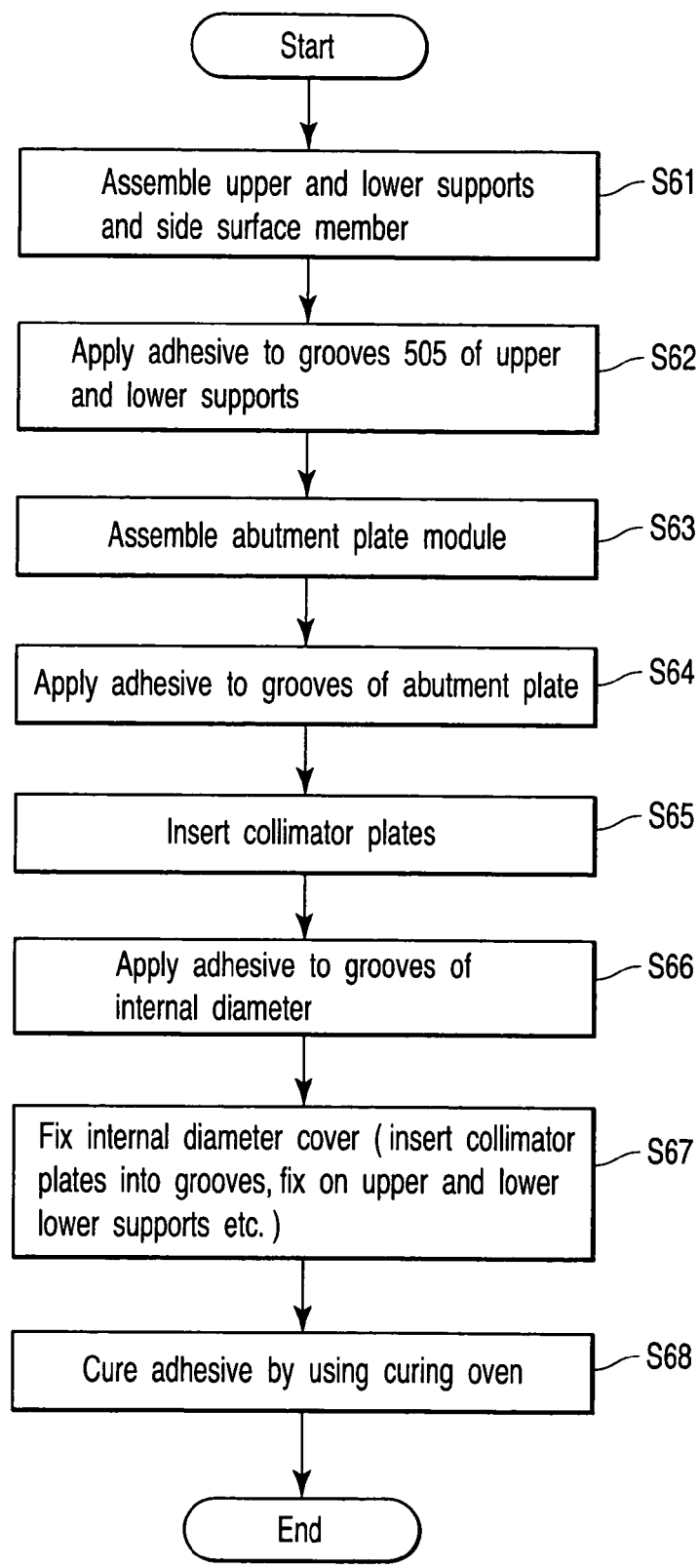
FIG. 26 is a flow chart showing the flow of a manufacturing process for the detector-side collimator 50 according to the fifth embodiment.

FIG. 26 is a flowchart showing the flow of a manufacturing process for the detector-side collimator 50. As illustrated, first, the upper support 500, lower support 501 and side surface members 502 are assembled to form an outer frame of the X-ray detector-side collimator 50 (step S61). Then, an adhesive is applied to grooves 505 formed respectively on the upper support 500 and lower support 501 (step S62), and each modularized abutment plate 540 is resiliently deformed in a circular arc shape and assembled by, for example, a screw clamp on the arcuated side surface of the circumference-side of the upper support 500 and the lower support 501 (step S63).

An adhesive is then applied to the grooves 541 and 542 of each abutment plate 540 (step S64), and the collimator plates 504 are inserted in the grooves 505 of the upper support 500 and the lower support 501 and the grooves 541 of each abutment plate 540 (step S65).

Then, after an adhesive is applied to the grooves 521 of the internal diameter cover 520 (step S66), the internal diameter cover 520 is fixed on the upper support 500, the lower support 501 and the side surface members 502 while inserting each collimator plate 504 into each groove 521 (step S67). In addition, when inserting each collimator plate 504 into each groove 521, the internal diameter cover 520 may be pressed along the inserting direction, or may be pressed while causing at least either one of the collimator plate 504-side and the internal diameter cover 520 to vibrate, according to need.

The collimator 50 is then placed in a curing oven to cure the adhesive (step S68). As a result of each process above, the detector-side collimator 50 in which the four sides of each collimator plate 504 is being supported by the grooves 505, 521, 541 and 542 is completed.

MODIFIED EXAMPLES

Next, modified examples of the present embodiment will be explained. A detector-side collimator 50 according to the present modified example supports one side among the four sides of a collimator signal plate 504 by an internal diameter cover 525, which does not have grooves 521.

Figure 27:
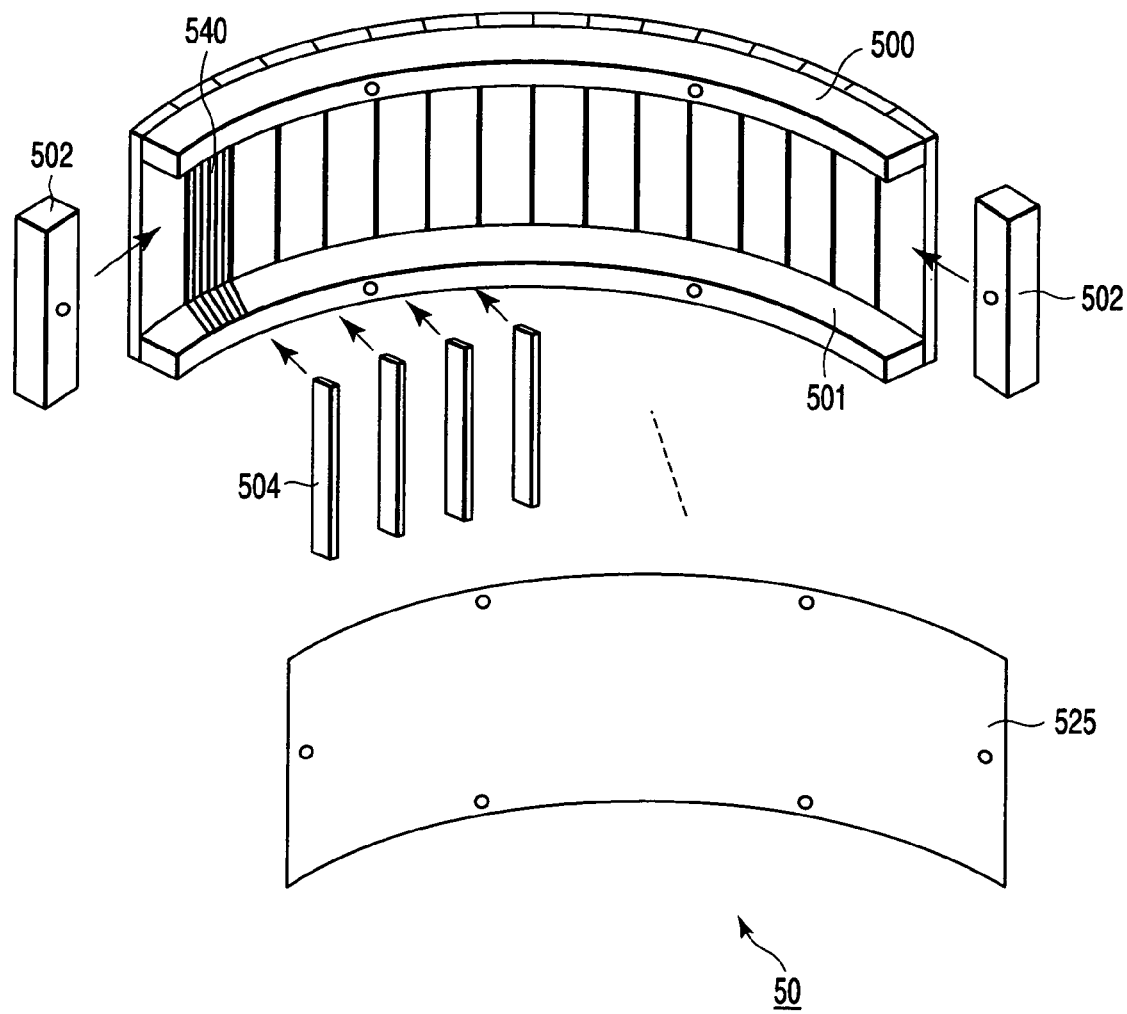
FIG. 27 is a view showing the arrangement of the detector-side collimator 50 according to a modified example of the fifth embodiment.

FIG. 27 is a view showing the arrangement of the detector-side collimator 50 according to the present modified example. As illustrated, the detector-side collimator 50 comprises a modularized abutment plate 540 and an internal diameter cover 525, which is integral and does not have grooves for inserting collimator plates 504.

(Collimator Manufacturing Method)

A method of manufacturing the detector-side collimator 50 according to the present modified example will be described next.

Figure 28:
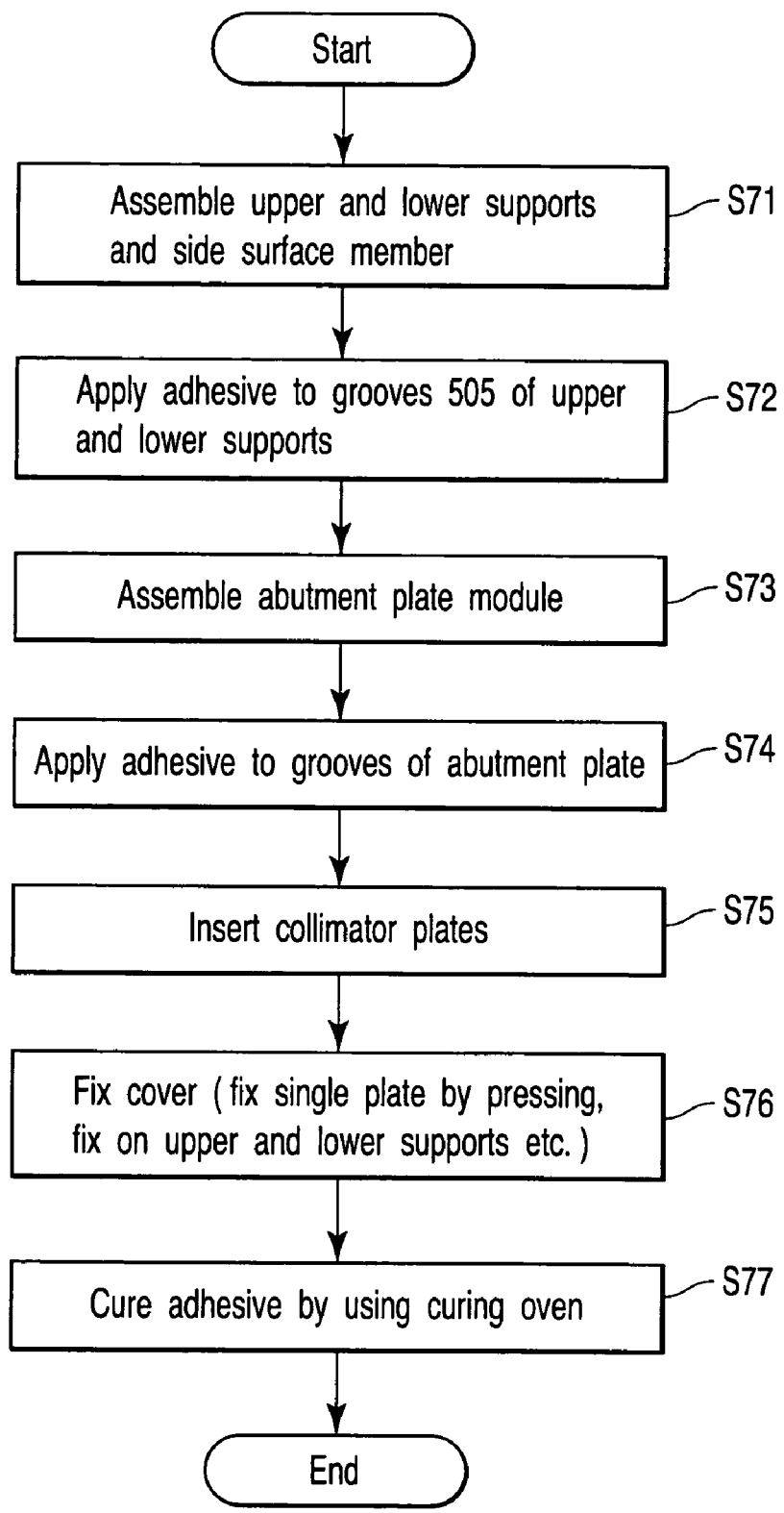
FIG. 28 is a flow chart showing the flow of a manufacturing process for the detector-side collimator 50 according to the modified example of the fifth embodiment.

FIG. 28 is a flowchart showing the flow of a manufacturing process for the detector-side collimator 50. Since the process from steps S71 to S75 is basically the same as the process from steps S61 to S65 shown in FIG. 26, description thereof will be omitted.

After the collimator plates 504 are inserted, the internal diameter cover 525 is fixed on the upper support 500, lower support 501 and side surface members 502 in a manner which presses one side of the X-ray tube 101-side of each collimator plate 504 (step S76).

The collimator 50 is then placed in a curing oven to cure the adhesive (step S77). As a result of each process above, the detector-side collimator 50 in which the four sides of each collimator plate 504 is being supported by the grooves 505 and 541 and the internal diameter cover 525 is completed.

According to the above arrangement, the next new effect can be realized in addition to the effect described in the third embodiment. In other words, being modularized, the abutment plate supporting one side of the collimator plate can be partially disassembled. Accordingly, when there is need to, for example, adjust or change a portion of the collimator plate, this may be done by only removing the abutment plate supporting such collimator plate. Consequently, this can reduce operation loads and expenses upon maintenance.

SIXTH EMBODIMENT

A detector-side collimator according to the sixth embodiment of the present invention, and an X-ray CT apparatus comprising such collimator will be described. The present detector-side collimator has a structure in which each collimator plate is supported by four sides, with an upper support, a lower support, an abutment plate and upper and lower internal diameter covers.

FIG. 29 is a view showing the arrangement of a detector-side collimator 50 possessed by an X-ray CT apparatus 10 according to the sixth embodiment. As illustrated, the detector-side collimator 50 according to the present embodiment comprises an upper support 500, a lower support 501, side surface members 502, an abutment plate 503, an integral upper internal diameter cover 550, an integral lower internal diameter cover 551 and a plurality of collimator plates 504.

The upper internal diameter cover 550 and the lower internal diameter cover 551 are plates which each bears an arcuated shape corresponding to the curvature (i.e., the curvature of an arc) of the upper support 500 and the lower support 501 in the channel direction. The upper internal diameter cover 550 is a cover that supports the collimator plate 504 from the internal diameter side of the upper support 500 and has a groove 552 to insert one side of the collimator plate 504. Likewise the abutment plate 503, the upper internal diameter cover 550 and lower internal diameter cover 551 are made of a material exhibiting high X-ray resistance, processability, X-ray transparency, and mechanical structural strength, such as polyethylene terephthalate, an epoxy resin, or a carbon fiber resin.

In addition, the upper internal diameter cover 550 and the lower internal diameter cover 551 can be made by basically the same method as for making the internal diameter cover 520 according to the third embodiment.

(Collimator Manufacturing Method)

A method of manufacturing the detector-side collimator 50 according to the present embodiment will be described next.

Figure 30:
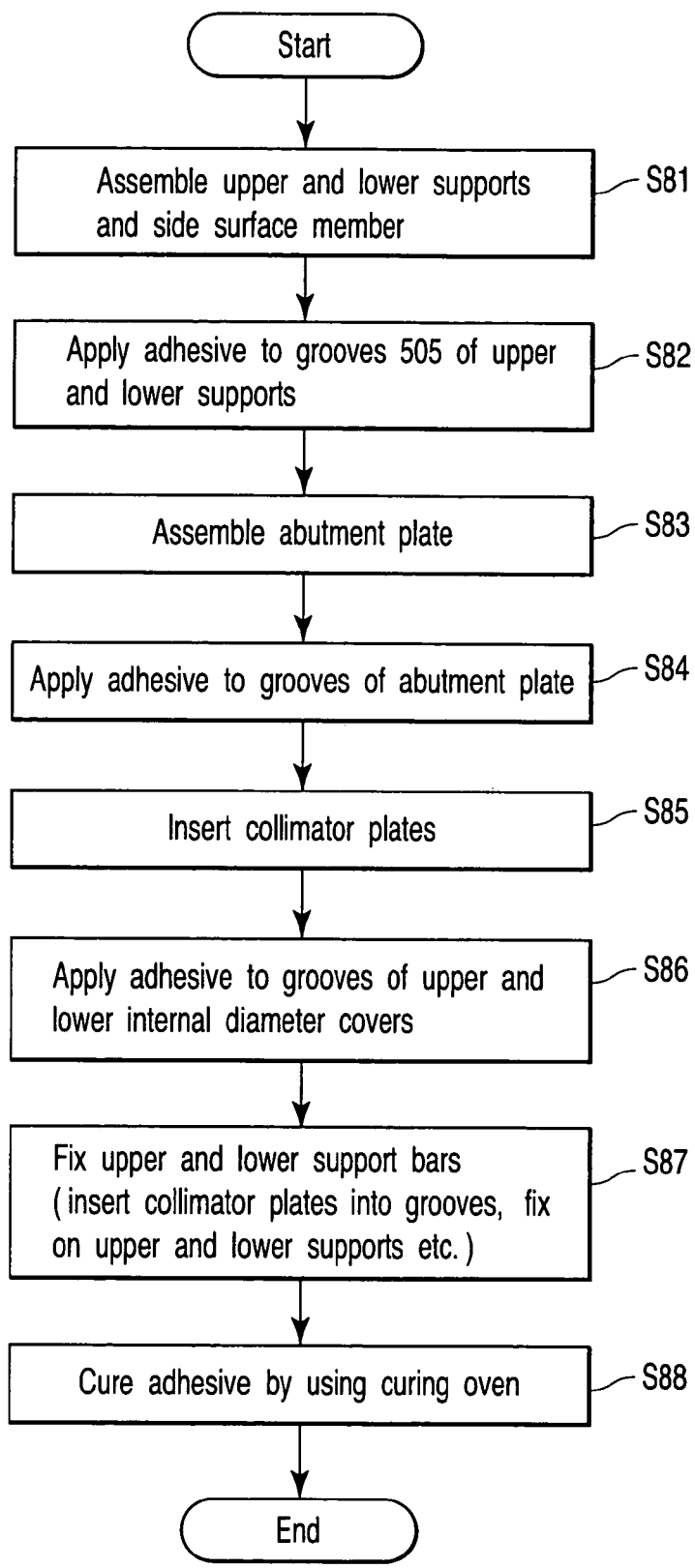
FIG. 30 is a flow chart showing the flow of a manufacturing process for the detector-side collimator 50 according to the sixth embodiment.

FIG. 30 is a flowchart showing the flow of a manufacturing process for the detector-side collimator 50. The process from steps S81 to S85 is basically the same as the process from steps S21 to S25 shown in FIG. 16, and hence a description thereof will be omitted.

After inserting the collimator plates 504, an adhesive is applied to grooves 552 on the upper internal diameter cover 550 (step S86), which is then fixed on the upper support 500 and side surface members 502 while inserting each collimator plate 504 in each groove 552. Further, an adhesive is applied to grooves 552 on the lower internal diameter cover 551, which is then fixed on the lower support 501 and side surface members 502 while inserting each collimator plate 504 in each groove 552 (step S87). Meanwhile, when inserting each collimator plate 504 in each groove 552, the upper internal diameter cover 550 (lower internal diameter cover 551) may be pressed along the inserting direction or may be pressed while causing at least either one of the collimator plate 504-side and the internal diameter cover 550 to vibrate, according to need.

The collimator 50 is then placed in a curing oven to cure the adhesive (step S88). As a result of each process above, the detector-side collimator 50 in which the four sides of each collimator plate 504 is supported by the grooves 505, 506 and 552 is completed.

MODIFIED EXAMPLES

Next, modified examples of the present embodiment will be explained. A detector-side collimator 50 according to the present modified example supports one side among the four sides of a collimator signal plate 504 by an upper internal diameter cover 555 and a lower internal diameter cover 556 which do not have grooves 552.

Figure 31:
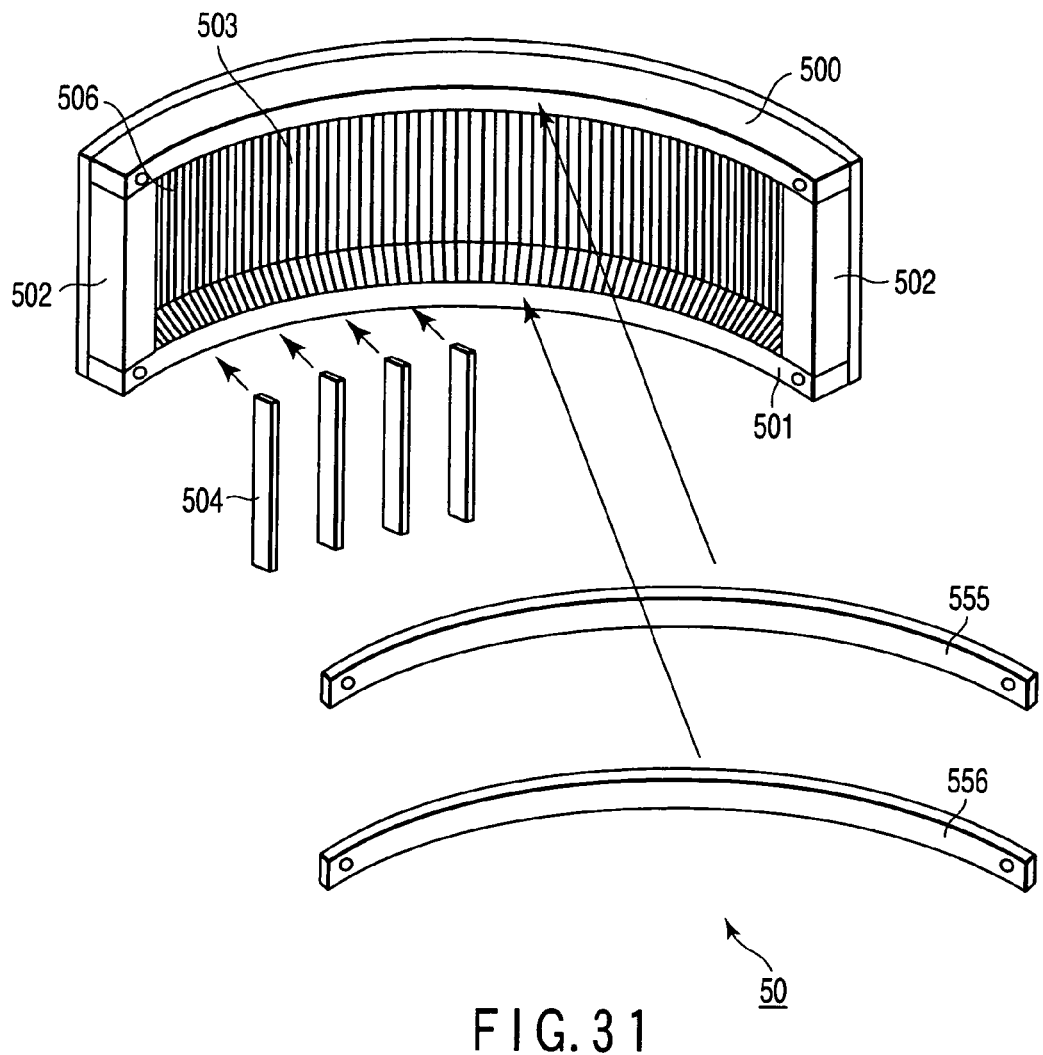
FIG. 31 is a view showing the arrangement of the detector-side collimator 50 according to a modified example of the sixth embodiment.

FIG. 31 is a view showing the arrangement of the detector-side collimator 50 according to the present modified example. As illustrated, the detector-side collimator 50 comprises an upper internal diameter cover 555 and lower internal diameter cover 556, which do not have grooves for inserting collimator plates 504.

Figure 32:
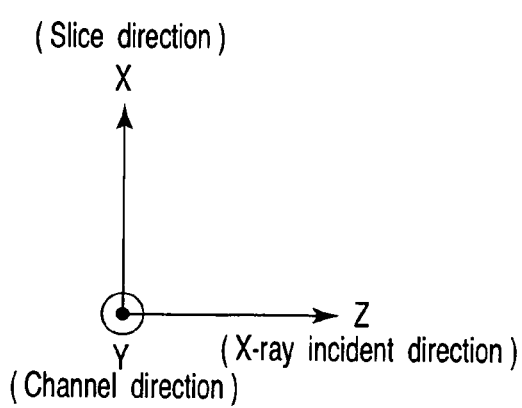
FIG. 32 is a view showing the arrangement of the detector-side collimator 50 according to the modified example of the sixth embodiment.
Figure 32:
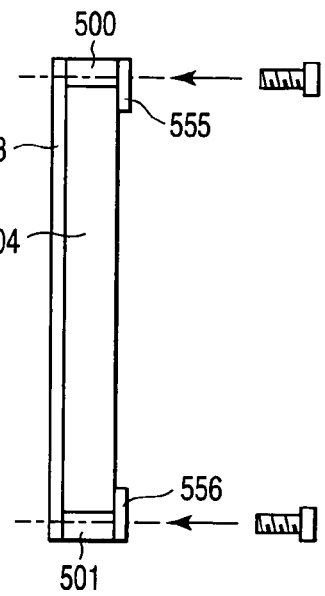

Except for the point that there are no grooves 552 formed on the upper internal diameter cover 555 and lower internal diameter cover 556, they have the same structures as the upper internal diameter cover 550 and the lower internal diameter cover 551. Likewise the example shown in FIG. 32, the upper internal diameter cover 555 and lower internal diameter cover 556 are fixed on the upper support 500 and so forth in a manner that presses one side of each collimator plate 504 (i.e., one side of the X-ray tube 101-side). Pressed by the upper internal diameter cover 555 and the lower internal diameter cover 556, the collimator plate 504 has the one side supported.

(Collimator Manufacturing Method)

A method of manufacturing the detector-side collimator 50 according to the present modified example will be described next.

Figure 33:
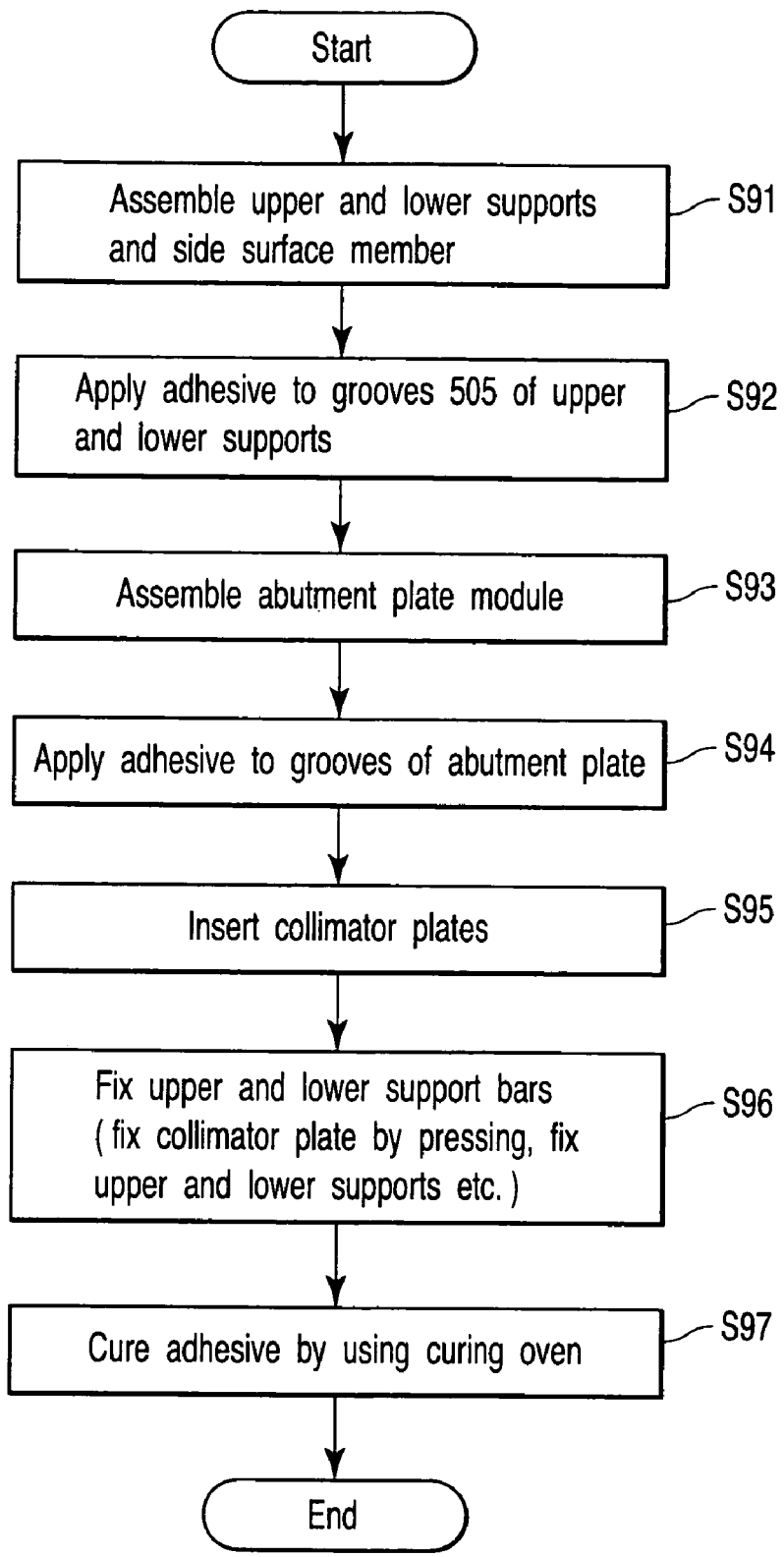
FIG. 33 is a flow chart showing the flow of a manufacturing process for the detector-side collimator 50 according to the modified example of the sixth embodiment.

FIG. 33 is a flowchart showing the flow of a manufacturing process for the detector-side collimator 50. Since the process from steps S91 to S95 is basically the same as the process from steps S81 to S85 shown in FIG. 30, description thereof will be omitted.

After inserting the collimator plates 504, the upper internal diameter cover 555 is fixed on the upper support 500 and side surface members 502 so as to press one side of the X-ray tube 101-side of each collimator plate 504. Further, the lower internal diameter cover 556 is fixed on the lower support 501 and side surface members 502 so as to press one side of the X-ray tube 101-side of each collimator plate 504 (step S96).

The collimator 50 is then placed in a curing oven to cure the adhesive (step S97). As a result of each process above, the detector-side collimator 50 in which the four sides of each collimator plate 504 is supported by the grooves 505 and 506, the upper internal diameter cover 555 and lower internal diameter cover 556 is completed.

According to the above arrangement, an effect equivalent to the third embodiment can be realized.

Note that the present invention is not limited to the above embodiments, and constituent elements can be modified and embodied in the execution stage within the spirit and scope of the invention.

(1) The guide plate 510 described in the second embodiment comprises the integral member which covers the upper support 500 and the lower support 501 (see FIGS. 9 and 10). However, the present invention is not limited to this. In consideration of, for example, limitations in terms of groove processing, this guide plate may have a split structure which covers the upper support 500 and the lower support 501 with a plurality of plates. If a split arrangement is to be used, the joint portions are preferably tapered to overlap each other or placed at the shadows of the collimator plates as in the case of the abutment plate 503.

(2) The abutment plate 503 and guide plate 510 described in each embodiment may be applied to a module type collimator. This makes it possible to maintain the flatness of each collimator plate in a module type collimator with higher accuracy than in the prior art.

(3) The detector-side collimator described in each embodiment may comprise a plurality of (e.g., three or four) collimator units (50) coupled to each other instead of a completely integral structure. In this case, the arrangements described in the respective embodiments and modifications (1) and (2) can be applied to each collimator unit (50).

(4) The detector-side collimator according to the sixth embodiment may be arranged to modularize at least either one of the upper internal diameter cover and the lower internal diameter cover as shown, for example, in FIG. 34.

In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

What is claimed is:

1. An X ray computer tomography apparatus comprising:

an X ray emitting unit which emits X rays;

an X ray detection unit which is placed to face the X ray emitting unit and detects X rays incident to a detection surface; and a collimator unit which is placed on the X ray incident side of an X ray detector to remove scattered X rays and includes a plurality of collimator plates and a support unit, the plurality of collimator plates being arranged along a predetermined direction, and the support unit supporting each of the collimator plates along at least three sides thereof in such a manner that a surface of each of the collimator plates is substantially parallel to an X ray incident direction from the X ray emitting unit to the detection surface;

wherein:

the support unit includes:

a first support member which includes a plurality of first grooves provided along the predetermined direction, each of the first grooves being formed along the X ray incident direction;

a second support member which is placed parallel to the first support unit and includes a plurality of second grooves provided along the predetermined direction so as to correspond to said plurality of first grooves, each of the second grooves being formed along the X ray incident direction; and a third support member which includes a plurality of third grooves for fitting of detection surface side peripheries of the collimator plates fitted in the first grooves and the second grooves, and is provided on the detection surface side of the plurality of collimator plates;

wherein the support unit further comprises a fourth support member which includes a plurality of fourth grooves for fitting of X ray emitting unit side peripheries of the collimator plates fitted in the first grooves and the second grooves, and is provided on the X ray emitting unit side of the plurality of collimator plates.

2. An X ray computer tomography apparatus according to claim 1, wherein the support unit includes the third support members which are modularized.

3. An X ray computer tomography apparatus according to claim 2, wherein each of the third support members further includes a fifth groove which form the third groove for inserting the collimator plate between the neighboring the third support members when the third support members are arrayed along the predetermined direction.

4. An X ray computer tomography apparatus comprising:

an X ray emitting unit which emits X rays;

an X ray detection unit which is placed to face the X ray emitting unit and detects X rays incident to a detection surface; and a collimator unit which is placed on the X ray incident side of an X ray detector to remove scattered X rays and includes a plurality of collimator plates and a support unit, the plurality of collimator plates being arranged along a predetermined direction, and the support unit supporting each of the collimator plates along at least three sides thereof in such a manner that a surface of each of the collimator plates is substantially parallel to an X ray incident direction from the X ray emitting unit to the detection surface;

wherein:

the support unit includes:

a first support member which includes a plurality of first grooves provided along the predetermined direction, each of the first grooves being formed along the X ray incident direction;

a second support member which is placed parallel to the first support unit and includes a plurality of second grooves provided along the predetermined direction so as to correspond to said plurality of first grooves, each of the second grooves being formed along the X ray incident direction; and a third support member which includes a plurality of third grooves for fitting of detection surface side peripheries of the collimator plates fitted in the first grooves and the second grooves, and is provided on the detection surface side of the plurality of collimator plates;

wherein the support unit further comprises a fourth support member which supports the plurality of the plates by pressing X-ray emitting unit side peripheries of the collimator plates fitted in the first grooves and the second grooves, and is provided on the X ray emitting unit side of the plurality of collimator plates.

5. An X ray computer tomography apparatus according to claim 4, wherein the support unit includes the third support members which are modularized.

6. An X ray computer tomography apparatus according to claim 5, wherein each of the third support members further includes a fifth groove which form the third groove between the neighboring the third support members for inserting the collimator plate when the third support members are arrayed along the predetermined direction.

7. An X ray computer tomography apparatus according to claim 1, wherein each of the fourth support members further includes a fifth groove which form the fourth groove between the neighboring fourth support members for inserting the collimator plate when the third support members are arrayed along the predetermined direction.

8. An X ray computer tomography apparatus comprising:

an X ray emitting unit which emits X rays;

an X ray detection unit which is placed to face the X ray emitting unit and detects X rays incident to a detection surface; and a collimator unit which is placed on the X ray incident side of an X ray detector to remove scattered X rays and includes a plurality of collimator plates and a support unit, the plurality of collimator plates being arranged along a predetermined direction, and the support unit supporting each of the collimator plates along at least three sides thereof in such a manner that a surface of each of the collimator plates is substantially parallel to an X ray incident direction from the X ray emitting unit to the detection surface;

wherein:

the support unit includes:

a first support member which includes a plurality of first grooves provided along the predetermined direction, each of the first grooves being formed along the X ray incident direction;

a second support member which is placed parallel to the first support unit and includes a plurality of second grooves provided along the predetermined direction so as to correspond to said plurality of first grooves, each of the second grooves being formed along the X ray incident direction; and a third support member which includes a plurality of third grooves for fitting of detection surface side peripheries of the collimator plates fitted in the first grooves and the second grooves, and is provided on the detection surface side of the plurality of collimator plates;

wherein the support unit further comprises a fourth support member which supports the plurality of the plates by pressing the X-ray emitting unit side peripheries of the collimator plates fitted in the first grooves and the second grooves, are modularized and are provided on the X ray emitting unit side of the plurality of collimator plates.

9. An X ray computer tomography apparatus comprising:

an X ray emitting unit which emits X rays;

an X ray detection unit which is placed to face the X ray emitting unit and detects X rays incident to a detection surface; and a collimator unit which is placed on the X ray incident side of an X ray detector to remove scattered X rays and includes a plurality of collimator plates and a support unit, the plurality of collimator plates being arranged along a predetermined direction, and the support unit supporting each of the collimator plates along at least three sides thereof in such a manner that a surface of each of the collimator plates is substantially parallel to an X ray incident direction from the X ray emitting unit to the detection surface;

wherein:

the support unit includes:

a first support member which includes a plurality of first grooves provided along the predetermined direction, each of the first grooves being formed along the X ray incident direction;

a second support member which is placed parallel to the first support unit and includes a plurality of second grooves provided along the predetermined direction so as to correspond to said plurality of first grooves, each of the second grooves being formed along the X ray incident direction; and a third support member which includes a plurality of third grooves for fitting of detection surface side peripheries of the collimator plates fitted in the first grooves and the second grooves, and is provided on the detection surface side of the plurality of collimator plates;

wherein the support unit further includes:

a fourth support member which includes a plurality of fourth grooves for fitting of the X-ray emitting unit side peripheries of the collimator plates fitted in the first grooves, and is provided on the X ray emitting unit side of the plurality of collimator plates; and a fifth support member which includes a plurality of fifth grooves for fitting of the X-ray emitting unit side peripheries of the collimator plates fitted in the second grooves, and is provided on the X ray emitting unit side of the plurality of collimator plates.

10. An X ray computer tomography apparatus comprising:

an X ray emitting unit which emits X rays;

an X ray detection unit which is placed to face the X ray emitting unit and detects X rays incident to a detection surface; and a collimator unit which is placed on the X ray incident side of an X ray detector to remove scattered X rays and includes a plurality of collimator plates and a support unit, the plurality of collimator plates being arranged along a predetermined direction, and the support unit supporting each of the collimator plates along at least three sides thereof in such a manner that a surface of each of the collimator plates is substantially parallel to an X ray incident direction from the X ray emitting unit to the detection surface;

wherein:
the support unit includes:
a first support member which includes a plurality of first grooves provided along the predetermined direction, each of the first grooves being formed along the X ray incident direction;
a second support member which is placed parallel to the first support unit and includes a plurality of second grooves provided along the predetermined direction so as to correspond to said plurality of first grooves, each of the second grooves being formed along the X ray incident direction; and
a third support member which includes a plurality of third grooves for fitting of detection surface side peripheries of the collimator plates fitted in the first grooves and the second grooves, and is provided on the detection surface side of the plurality of collimator plates;
wherein the support unit further includes:
a fourth support member which supports the plurality of the plates by pressing the X-ray emitting unit side peripheries of the collimator plates fitted in the first grooves, and is provided on the X ray emitting unit side of the plurality of collimator plates and along the first supporting member; and
a fifth support member which supports the plurality of the plates by pressing the X-ray emitting unit side peripheries of the collimator plates fitted in the second grooves, and is provided on the X ray emitting unit side of the plurality of collimator plates along the second supporting member.

11. An X ray computer tomography apparatus comprising:
an X ray emitting unit which emits X rays;
an X ray detection unit which is placed to face the X ray emitting unit and detects X rays incident to a detection surface; and
a collimator unit which is placed on the X ray incident side of an X ray detector to remove scattered X rays and includes a plurality of collimator plates and a support unit, the plurality of collimator plates being arranged along a predetermined direction, and the support unit supporting each of the collimator plates along at least three sides thereof in such a manner that a surface of each of the collimator plates is substantially parallel to an X ray incident direction from the X ray emitting unit to the detection surface;
wherein:
the support unit includes:
a first support member which includes a plurality of first grooves provided along the predetermined direction, each of the first grooves being formed along the X ray incident direction;
a second support member which is placed parallel to the first support unit and includes a plurality of second grooves provided along the predetermined direction so as to correspond to said plurality of first grooves, each of the second grooves being formed along the X ray incident direction; and
a third support member which includes a plurality of third grooves for fitting of detection surface side peripheries of the collimator plates fitted in the first grooves and the second grooves, and is provided on the detection surface side of the plurality of collimator plates;
further comprising a fourth support unit which includes slits which support peripheries of the collimator plates on the X ray emitting unit side and allow the collimator plates fitted in the first grooves and the second grooves which face each other to pass through and is provided on the X ray emitting unit side of the collimator.

12. A collimator which is used for an X ray computer tomography apparatus comprising an X ray emitting unit which emits X rays and an X ray detection unit which is placed to face the X ray exposing unit and detects X rays striking a detection surface, and is provided on the detection surface side to remove scattered X rays, comprising:
a plurality of collimator plates being arranged along a predetermined direction; and
a support unit supporting each of the collimator plates along at least three sides thereof in such a manner that a surface of each of the collimator plates is substantially parallel to an X ray incident direction from the X ray emitting unit to the detection surface;
wherein the support unit includes:
a first support member which includes a plurality of first grooves provided along the predetermined direction, each of the first grooves being formed along the X ray incident direction;
a second support member which is placed parallel to the first support unit and includes a plurality of second grooves provided along the predetermined direction so as to correspond to said plurality of first grooves, each of the second grooves being formed along the X ray incident direction; and
a third support member which includes a plurality of third grooves for fitting of detection surface side peripheries of the collimator plates fitted in the first grooves and the second grooves, and is provided on the detection surface side of the plurality of collimator plates;
wherein the support unit further comprises a fourth support member which includes a plurality of fourth grooves for fitting of X ray emitting unit side peripheries of the collimator plates fitted in the first grooves and the second grooves, and is provided on the X ray emitting unit side of the plurality of collimator plates.

13. A collimator which is used for an X ray computer tomography apparatus comprising an X ray emitting unit which emits X rays and an X ray detection unit which is placed to face the X ray exposing unit and detects X rays striking a detection surface, and is provided on the detection surface side to remove scattered X rays, comprising:
a plurality of collimator plates being arranged along a predetermined direction; and
a support unit supporting each of the collimator plates along at least three sides thereof in such a manner that a surface of each of the collimator plates is substantially parallel to an X ray incident direction from the X ray emitting unit to the detection surface;
wherein the support unit includes:
a first support member which includes a plurality of first grooves provided along the predetermined direction, each of the first grooves being formed along the X ray incident direction;
a second support member which is placed parallel to the first support unit and includes a plurality of second grooves provided along the predetermined direction so as to correspond to said plurality of first grooves, each of the second grooves being formed along the X ray incident direction; and
a third support member which includes a plurality of third grooves for fitting of detection surface side peripheries of the collimator plates fitted in the first grooves and the second grooves, and is provided on the detection surface side of the plurality of collimator plates;

wherein the support unit includes the third support members which are modularized, and each of the third support members further includes a fourth groove which forms the third groove for inserting the collimator plate between the neighboring the third support members when the third support members are arrayed along the predetermined direction.

14. A collimator which is used for an X ray computer tomography apparatus comprising an X ray emitting unit which emits X rays and an X ray detection unit which is placed to face the X ray exposing unit and detects X rays striking a detection surface, and is provided on the detection surface side to remove scattered X rays, comprising:
   a plurality of collimator plates being arranged along a predetermined direction; and
   a support unit supporting each of the collimator plates along at least three sides thereof in such a manner that a surface of each of the collimator plates is substantially parallel to an X ray incident direction from the X ray emitting unit to the detection surface;
   wherein the support unit includes:
   a first support member which includes a plurality of first grooves provided along the predetermined direction, each of the first grooves being formed along the X ray incident direction;
   a second support member which is placed parallel to the first support unit and includes a plurality of second grooves provided along the predetermined direction so as to correspond to said plurality of first grooves, each of the second grooves being formed along the X ray incident direction; and
   a third support member which includes a plurality of third grooves for fitting of detection surface side peripheries of the collimator plates fitted in the first grooves and the second grooves, and is provided on the detection surface side of the plurality of collimator plates;
   wherein the support unit further comprises a fourth support member which supports the plurality of the plates by pressing X-ray emitting unit side peripheries of the collimator plates fitted in the first grooves and the second grooves, and is provided on the X ray emitting unit side of the plurality of collimator plates.

15. A collimator according to claim 14, wherein the support unit includes the third support members which are modularized.

16. A collimator according to claim 15, wherein each of the third support members further includes a fifth groove which form the third groove between the neighboring the third support members for inserting the collimator plate when the third support members are arrayed along the predetermined direction.

17. A collimator according to claim 12, wherein each of the fourth support members further includes a fifth groove which form the fourth groove between the neighboring third support members for inserting the collimator plate when the fourth support members are arrayed along the predetermined direction.

18. A collimator which is used for an X ray computer tomography apparatus comprising an X ray emitting unit which emits X rays and an X ray detection unit which is placed to face the X ray exposing unit and detects X rays striking a detection surface, and is provided on the detection surface side to remove scattered X rays, comprising:
   a plurality of collimator plates being arranged along a predetermined direction; and
   a support unit supporting each of the collimator plates along at least three sides thereof in such a manner that a surface of each of the collimator plates is substantially parallel to an X ray incident direction from the X ray emitting unit to the detection surface;
   wherein the support unit includes:
   a first support member which includes a plurality of first grooves provided along the predetermined direction, each of the first grooves being formed along the X ray incident direction;
   a second support member which is placed parallel to the first support unit and includes a plurality of second grooves provided along the predetermined direction so as to correspond to said plurality of first grooves, each of the second grooves being formed along the X ray incident direction; and
   a third support member which includes a plurality of third grooves for fitting of detection surface side peripheries of the collimator plates fitted in the first grooves and the second grooves, and is provided on the detection surface side of the plurality of collimator plates;
   wherein the support unit further comprises a fourth support member which supports the plurality of the plates by pressing the X-ray emitting unit side peripheries of the collimator plates fitted in the first grooves and the second grooves, are modularized and are provided on the X ray emitting unit side of the plurality of collimator plates.

19. A collimator which is used for an X ray computer tomography apparatus comprising an X ray emitting unit which emits X rays and an X ray detection unit which is placed to face the X ray exposing unit and detects X rays striking a detection surface, and is provided on the detection surface side to remove scattered X rays, comprising:
   a plurality of collimator plates being arranged along a predetermined direction; and
   a support unit supporting each of the collimator plates along at least three sides thereof in such a manner that a surface of each of the collimator plates is substantially parallel to an X ray incident direction from the X ray emitting unit to the detection surface;
   wherein the support unit includes:
   a first support member which includes a plurality of first grooves provided along the predetermined direction, each of the first grooves being formed along the X ray incident direction;
   a second support member which is placed parallel to the first support unit and includes a plurality of second grooves provided along the predetermined direction so as to correspond to said plurality of first grooves, each of the second grooves being formed along the X ray incident direction; and
   a third support member which includes a plurality of third grooves for fitting of detection surface side peripheries of the collimator plates fitted in the first grooves and the second grooves, and is provided on the detection surface side of the plurality of collimator plates;
   wherein the support unit further comprises:
   a fourth support member which includes a plurality of fifth grooves for fitting of the X-ray emitting unit side peripheries of the collimator plates fitted in the first grooves, and is provided on the X ray emitting unit side of the plurality of collimator plates; and
   a fifth support member which includes a plurality of sixth grooves for fitting of the X-ray emitting unit side peripheries of the collimator plates fitted in the second grooves, and is provided on the X ray emitting unit side of the plurality of collimator plates.

20. A collimator which is used for an X ray computer tomography apparatus comprising an X ray emitting unit which emits X rays and an X ray detection unit which is placed to face the X ray exposing unit and detects X rays striking a detection surface, and is provided on the detection surface side to remove scattered X rays, comprising:

a plurality of collimator plates being arranged along a predetermined direction; and a support unit supporting each of the collimator plates along at least three sides thereof in such a manner that a surface of each of the collimator plates is substantially parallel to an X ray incident direction from the X ray emitting unit to the detection surface;

wherein the support unit includes:

a first support member which includes a plurality of first grooves provided along the predetermined direction, each of the first grooves being formed along the X ray incident direction;

a second support member which is placed parallel to the first support unit and includes a plurality of second grooves provided along the predetermined direction so as to correspond to said plurality of first grooves, each of the second grooves being formed along the X ray incident direction; and a third support member which includes a plurality of third grooves for fitting of detection surface side peripheries of the collimator plates fitted in the first grooves and the second grooves, and is provided on the detection surface side of the plurality of collimator plates;

wherein the support unit further comprises:

a fourth support member which supports the plurality of the plates by pressing the X-ray emitting unit side peripheries of the collimator plates fitted in the first grooves, and is provided on the X ray emitting unit side of the plurality of collimator plates and along the first supporting member; and a fifth support member which supports the plurality of the plates by pressing the X-ray emitting unit side peripheries of the collimator plates fitted in the second grooves, and is provided on the X ray emitting unit side of the plurality of collimator plates along the second supporting member.

21. A collimator which is used for an X ray computer tomography apparatus comprising an X ray emitting unit which emits X rays and an X ray detection unit which is placed to face the X ray exposing unit and detects X rays striking a detection surface, and is provided on the detection surface side to remove scattered X rays, comprising:

a plurality of collimator plates being arranged along a predetermined direction; and a support unit supporting each of the collimator plates along at least three sides thereof in such a manner that a surface of each of the collimator plates is substantially parallel to an X ray incident direction from the X ray emitting unit to the detection surface;

wherein the support unit includes:

a first support member which includes a plurality of first grooves provided along the predetermined direction, each of the first grooves being formed along the X ray incident direction;

a second support member which is placed parallel to the first support unit and includes a plurality of second grooves provided along the predetermined direction so as to correspond to said plurality of first grooves, each of the second grooves being formed along the X ray incident direction; and a third support member which includes a plurality of third grooves for fitting of detection surface side peripheries of the collimator plates fitted in the first grooves and the second grooves, and is provided on the detection surface side of the plurality of collimator plates;

further comprising a fourth support unit which includes slits which support peripheries of the collimator plates on the X ray emitting unit side and allow the collimator plates fitted in the first grooves and the second grooves which face each other to pass through and is provided on the X ray emitting unit side of the collimator.

22. An X ray computer tomography apparatus collimator manufacturing method of manufacturing a collimator which is used for an X ray computer tomography apparatus comprising an X ray emitting unit which emits X rays and an X ray detection unit which is placed to face the X ray emitting unit through a subject and detects X rays striking a detection surface, and is provided on the detection surface to remove scattered X rays, comprising:

assembling, by using side surface members, a first support unit including a plurality of first grooves formed along an X ray incident direction from the X ray emitting unit to the detection surface and a second support unit including a plurality of second grooves formed along the X ray incident direction from the X ray emitting unit to the detection surface so as to correspond to said plurality of first grooves;

fixing, to the detection surface side of the first support unit and second support unit, a third support unit including a plurality of third grooves for fitting of peripheries of the collimator plates fitted in the first grooves and the second grooves corresponding to each other which are located on the detection surface side;

fixing the second support unit including slits which allow the collimator plates fitted in the first grooves and the second grooves which face each other to pass through the slits and support peripheries of the collimator plates which are on an X ray incident side to the X ray incident side of the first support unit and the second support unit;

fitting collimator plates in the first grooves, the second grooves, and the third grooves upon making the collimator plates pass through the slits so as to support the collimator plates along at least three sides thereof; and bonding the collimator plates to the first grooves, the second grooves, the third grooves, and the slits which correspond to each other.

* * * * *